(12) United States Patent
Nakano et al.

(10) Patent No.: US 7,258,485 B2
(45) Date of Patent: Aug. 21, 2007

(54) X-RAY THIN FILM INSPECTION APPARATUS AND THIN FILM INSPECTION APPARATUS AND METHOD FOR PATTERNED WAFER

(75) Inventors: Asao Nakano, Kanagawa (JP); Takao Kinefuchi, Tokyo (JP); Hiroshi Motono, Tokyo (JP); Atsunori Kiku, Tokyo (JP)

(73) Assignee: Rigaku Corporation, Tokyo (JP)

( * ) Notice: Subject to any disclaimer, the term of this patent is extended or adjusted under 35 U.S.C. 154(b) by 113 days.

(21) Appl. No.: 11/259,191

(22) Filed: Oct. 26, 2005

(65) Prior Publication Data

US 2006/0088139 A1    Apr. 27, 2006

(30) Foreign Application Priority Data

Oct. 26, 2004 (JP) ............... 2004-311563
Nov. 30, 2004 (JP) ............... 2004-347686

(51) Int. Cl.
*H05G 1/02* (2006.01)
*A61B 6/08* (2006.01)
*G01N 23/20* (2006.01)
*G01N 23/223* (2006.01)

(52) U.S. Cl. .......... 378/205; 378/46; 378/71; 378/72; 378/73; 378/76; 378/79; 378/81; 378/196; 378/197; 378/208

(58) Field of Classification Search ........ 378/70, 378/71, 72, 73, 76, 79, 81, 86, 90, 196, 197, 378/205, 208, 209
See application file for complete search history.

(56) References Cited

U.S. PATENT DOCUMENTS 4,995,063 A * 2/1991 Enoki et al. ............... 378/70
6,005,914 A * 12/1999 Quinn et al. ............... 378/81
6,301,330 B1 * 10/2001 Kurtz et al. ............... 378/71
6,404,849 B1 * 6/2002 Olson et al. ............... 378/79
6,459,763 B1 * 10/2002 Koinuma et al. ............... 378/71
6,463,121 B1 * 10/2002 Milnes ............... 378/62
6,718,008 B1 * 4/2004 He et al. ............... 378/71
6,735,276 B2 * 5/2004 Ikeshita et al. ............... 378/45
6,859,520 B2 * 2/2005 He et al. ............... 378/79
6,909,772 B2 * 6/2005 Kozaczek et al. ............... 378/71
7,120,228 B2 * 10/2006 Yokhin et al. ............... 378/90
2001/0017878 A1 8/2001 Nozoe et al. ............... 374/5

FOREIGN PATENT DOCUMENTS

| JP | 10-325803 | 12/1998 |
|---|---|---|
| JP | 2003-529047 | 9/2003 |
| JP | 2004-037108 | 2/2004 |
| JP | 2004-170226 | 6/2004 |
| JP | 2004-233262 | 8/2004 |
| WO | WO-01/09566 | 2/2001 |

* cited by examiner

*Primary Examiner*—Allen C. Ho
(74) *Attorney, Agent, or Firm*—Jordan and Hamburg LLP

(57) ABSTRACT

An X-ray thin film inspection apparatus including a sample table on which an inspection target such as a product wafer or the like is mounted, a positioning mechanism for moving the sample table, a goniometer having first and second swing arms, at least one X-ray irradiation unit that are mounted on the first swing arm and containing an X-ray tube and an X-ray optical element in a shield tube, an X-ray detector mounted on a second swing arm, and an optical camera for subjecting the inspection target disposed on the sample table to pattern recognition.

18 Claims, 22 Drawing Sheets

Fig. 11

| MEASUREMENT TIME | FILM THICKNESS (Å) | DENSITY (g/cm³) |
|---|---|---|
| 300 sec | 498.9 | 5.41 |
| 15 sec | 500.9 | 5.31 |
| 6 sec | 500.0 | 5.35 |
| 3 sec | 497.3 | 5.27 |

X-RAY THIN FILM INSPECTION APPARATUS AND THIN FILM INSPECTION APPARATUS AND METHOD FOR PATTERNED WAFER

BACKGROUND OF THE INVENTION

1. Field of the Invention

The present invention relates to an X-ray thin film inspection apparatus suitable for a technical field of manufacturing a device having a multilayer film structure achieved by laminating many thin films on a substrate, such as a semiconductor manufacturing field.

2. Description of the Related Art

With respect to semiconductor devices or other types of devices in which a multilayer film structure achieved by laminating many thin films is formed on a substrate, the characteristics of these devices are varied in accordance with the film thickness, density, crystallinity, etc. of each thin film to be formed. Recently, the miniaturization and integration of these devices have been advanced, and this tendency has been remarkable. Therefore, a thin film inspection apparatus that can accurately measure the state of each film thus formed has been required.

Direct measurement by a sectional transmission electron microscope (TEM), a film thickness inspection apparatus using optical interference or ellipsometry, an opto-acoustic type apparatus, etc. have been hitherto known as this type of inspection apparatuses. With respect to the sectional transmission electron microscope (TEM), it is an actual condition that it is impossible to install the sectional transmission electron microscope in a manufacturing process and examine a thin film as an inspection target on a real-time basis, and also a product which is taken out from the manufacturing line for an inspection is discarded after the inspection. Furthermore, the film thickness inspection apparatus using optical interference or ellipsometry and the opto-acoustic type apparatus are suitable for the in-line process, however, the measurement precision thereof is too low to measure the thin film of several nm.

Wafers for inspection (blanket wafers) which are used once for inspection and then thrown away are a large cost load for semiconductor device makers. Particularly, the diameter of semiconductor wafers has been increased, and the cost needed for one blanket wafer has been also increased.

SUMMARY OF THE INVENTION

The present invention has been implemented in view of the foregoing situation, and has an object to provide an X-ray thin film inspection apparatus that is installed in a manufacturing process for film-formed products such as wafers to directly examine the products themselves and can inspect thin film formed in the products with sufficient precision without throwing away the products after the inspection even when the thickness of the thin film is in several nm level.

In order to attain the above object, according to a first aspect of the present invention, an X-ray thin film inspection apparatus comprises: a sample table for mounting an inspection target on the upper surface thereof; a pattern recognition unit for recognizing an image of the inspection target disposed on the upper surface of the sample table; a positioning mechanism that is controlled on the basis of a pattern recognition result of the inspection target achieved by the pattern recognition unit and moves the sample table in two directions orthogonal to each other on any plane, a direction perpendicular to the plane concerned and an in-plane rotational direction of the plane concerned; a goniometer having first and second swing members swinging along a virtual plane perpendicular to the upper surface of the sample table; at least one X-ray irradiation unit that is mounted on the first swing member and has an X-ray tube and an X-ray optical element mounted in the main body of the X-ray irradiation unit; and an X-ray detector mounted on the second swing member.

Here, in the above X-ray thin film inspection apparatus, it is preferable that the X-ray optical element of the X-ray irradiation unit has a function of leading X-rays irradiated from the X-ray tube to a preset measurement position while converging the X-rays thus irradiated into a cross-sectional shape of 200 µm or less in diameter.

Furthermore, in the above X-ray thin film inspection apparatus, the X-ray irradiation unit has a shutter for interrupting or passing therethrough the X-rays irradiated from the X-ray tube to lead the X-rays to the X-ray optical element in the main body of the X-ray irradiation unit, and a gas flow passage is formed around the shutter.

In the above X-ray thin film inspection apparatus, it is preferable that the X-ray detector comprises an avalanche photodiode (APD). For example, the avalanche photodiode can measure X-ray intensity of 10,000,000 counts or more per a second by one pixel of the X-ray detector element without using any means of attenuating the X-ray intensity.

Furthermore, in the above X-ray thin film inspection apparatus, plural X-ray irradiation units may be mounted on the first swing member so as to be arranged in the swing direction.

In the above X-ray thin film inspection apparatus, it is further preferable that the plural X-ray irradiation units contain X-ray tubes for generating X-rays having different wavelengths.

The X-ray thin film inspection apparatus according to the present invention may be further equipped with a fluorescent X-ray detector for detecting fluorescent X-rays generated from the inspection target by irradiating X-rays.

In the above X-ray thin film inspection apparatus, the pattern recognition unit may comprise an optical camera, and an pattern recognition circuit for recognizing an image taken by the optical camera.

In the above X-ray thin film inspection apparatus, the optical camera and the fluorescent X-ray detector may be attached above the sample table, and the X-ray thin film inspection apparatus may be further equipped with an equipment exchange mechanism for selecting one of the optical camera and the fluorescent X-ray detector and moving the selected one element of the optical camera and the fluorescent X-ray detector so that the selected one element faces a predetermined measurement position.

In this case, it is preferable that the X-ray thin film inspection apparatus is further equipped with a cover member for covering the optical camera, the fluorescent X-ray detector and the equipment exchange mechanism, the cover member being formed with a transmission window so that the transmission window faces the visual field of the optical camera, and an exhaust unit for air-flow to prevent dusts in the inner space formed by the cover.

Furthermore, in the above X-ray thin film inspection apparatus, the inspection target is a product wafer on which a plurality of semiconductor devices having the same structure including various kinds of minute thin film patterns are formed, a minute thin film pattern of a predetermined semiconductor device formed on the wafer concerned is set as a measurement target site, and the X-ray thin film inspection apparatus is further equipped with a controller for controlling the positioning mechanism on the basis of a recognition result from the pattern recognition unit to position the measurement target site to a predetermined measurement position and carrying out thin film inspection on the measurement target site.

Here, the controller further controls the positioning mechanism on the basis of the recognition result from the pattern recognition unit to position the measurement target site so that the longitudinal direction of the measurement target site is coincident with the incident direction of the X-rays from the X-ray irradiation unit.

When the inspection result of the measurement target site is out of a predetermined normal range which is judged as being normal, the controller may set the same measurement target site of the same thin film pattern of the same semiconductor device on the product wafer as a new measurement target site and carry out thin film inspection on the measurement target site thus newly set again.

When the inspection result of the measurement target site is out of a predetermined normal range which is judged as being normal, the controller sets any site of the same thin film pattern of a different semiconductor device on the product wafer as a measurement target site, controls the positioning mechanism on the basis of the recognition result from the pattern recognition unit to position the measurement target site to a predetermined measurement position, and carries out thin film inspection on the measurement target site.

According to a second aspect of the present invention, a product wafer thin film inspection apparatus comprises: an X-ray thin film inspection apparatus including a sample table for mounting an inspection target on the upper surface thereof, a pattern recognition unit for recognizing a pattern image of the inspection target mounted on the upper surface of the sample table, a positioning mechanism that is controlled on the basis of a pattern recognition result of the inspection target achieved by the pattern recognition unit and moves the sample table in two directions orthogonal to each other on any plane, a direction perpendicular to the plane concerned and an in-plane rotational direction of the plane concerned, a goniometer having first and second swing members swinging along a virtual plane perpendicular to the upper surface of the sample table, at least one X-ray irradiation unit that is mounted on the first swing member and has an X-ray tube and an X-ray optical element mounted in the main body of the X-ray irradiation unit, and an X-ray detector mounted on the second swing member; a feeding robot for feeding thin-film-formed semiconductor wafers in a semiconductor manufacturing process to the sample table of the X-ray thin film inspection apparatus one by one; and a mount cover in which the X-ray thin film inspection apparatus and the feeding robot are accommodated.

According to a third aspect of the present invention, a product wafer thin film inspection method using an X-ray thin film inspection apparatus including a sample table for disposing an inspection target on the upper surface thereof, a pattern recognition unit for recognizing an image of the inspection target disposed on the upper surface of the sample table, a positioning mechanism that is controlled on the basis of a pattern recognition result of the inspection target achieved by the pattern recognition unit and moves the sample table in two directions orthogonal to each other on any plane, a direction perpendicular to the plane concerned and an in-plane rotational direction of the plane concerned, a goniometer having first and second swing members swinging along a virtual plane perpendicular to the upper surface of the sample table, at least one X-ray irradiation unit that is mounted on the first swing member and has an X-ray tube and an X-ray optical element mounted in the main body of the X-ray irradiation unit, and an X-ray detector mounted on the second swing member, comprises the steps of setting a minute thin film pattern of a semiconductor device formed on a product wafer as a measurement target site; positioning the measurement target site to a measurement position of the X-ray thin film inspection apparatus; and carrying out thin film inspection on the measurement target site.

In the product wafer thin film inspection method described above, it is preferable that the thin film inspection of the measurement target site is carried out while the longitudinal direction of the measurement target site is coincident with the incident direction of the X-rays from the X-ray irradiation unit.

In the above X-ray thin film inspection method, it is preferable that when the inspection result of the measurement target site is out of a predetermined normal range which is judged as being normal, the same measurement target site of the same thin film pattern of the same semiconductor device on the product wafer is set as a new measurement target site and thin film inspection is carried out on the measurement target site thus newly set again.

In the above X-ray thin film inspection method, it is preferable that when the inspection result of the measurement target site is out of a predetermined normal range which is judged as being normal, any site of the same thin film pattern of a different semiconductor device on the product wafer is set as a measurement target site, the positioning mechanism is controlled on the basis of the recognition result from the pattern recognition unit to position the measurement target site to a predetermined measurement position, and thin film inspection is carried out on the measurement target site.

According to the present invention, there can be provided the X-ray thin film inspection apparatus that can be installed in the manufacturing process of film-formed products and with which direct inspection can be carried out on the products themselves and even thin film of several nm level in thickness can be examined with sufficient precision without throwing away a wafer after inspection.

BRIEF DESCRIPTION OF THE DRAWINGS

FIG. 11 is a graph showing inspection results of thin film thickness and film density inspection which was carried out by using XRR of 2θ-value from 0 to 3 degrees when the inspection apparatus of the present invention is used and the measurement time is varied;

DETAILED DESCRIPTION OF THE PREFERRED EMBODIMENTS

Preferred embodiments according to the present invention will be described hereunder in detail with reference to the accompanying drawings when the present invention is applied to thin film inspection of a semiconductor wafer.

It is needless to say that the present invention is not limited to thin film inspection of semiconductor wafers, but it may be applied to thin film inspection of various kinds of devices having a multilayer film structure achieved by laminating many thin films on a substrate.

Figure 1:
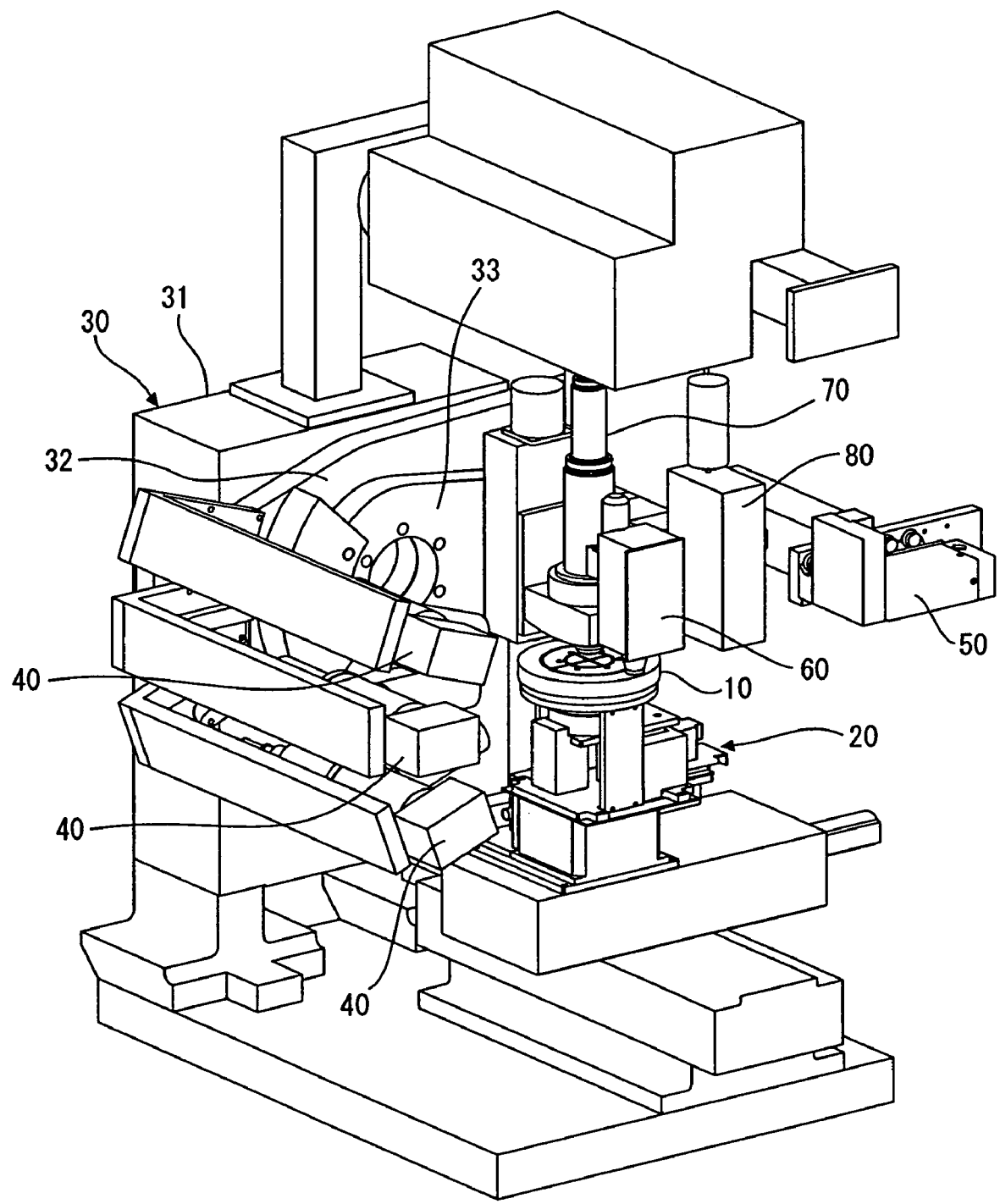
FIG. 1 is a perspective view showing the overall structure of an X-ray thin film inspection apparatus according to an embodiment of the present invention.
Figure 2:
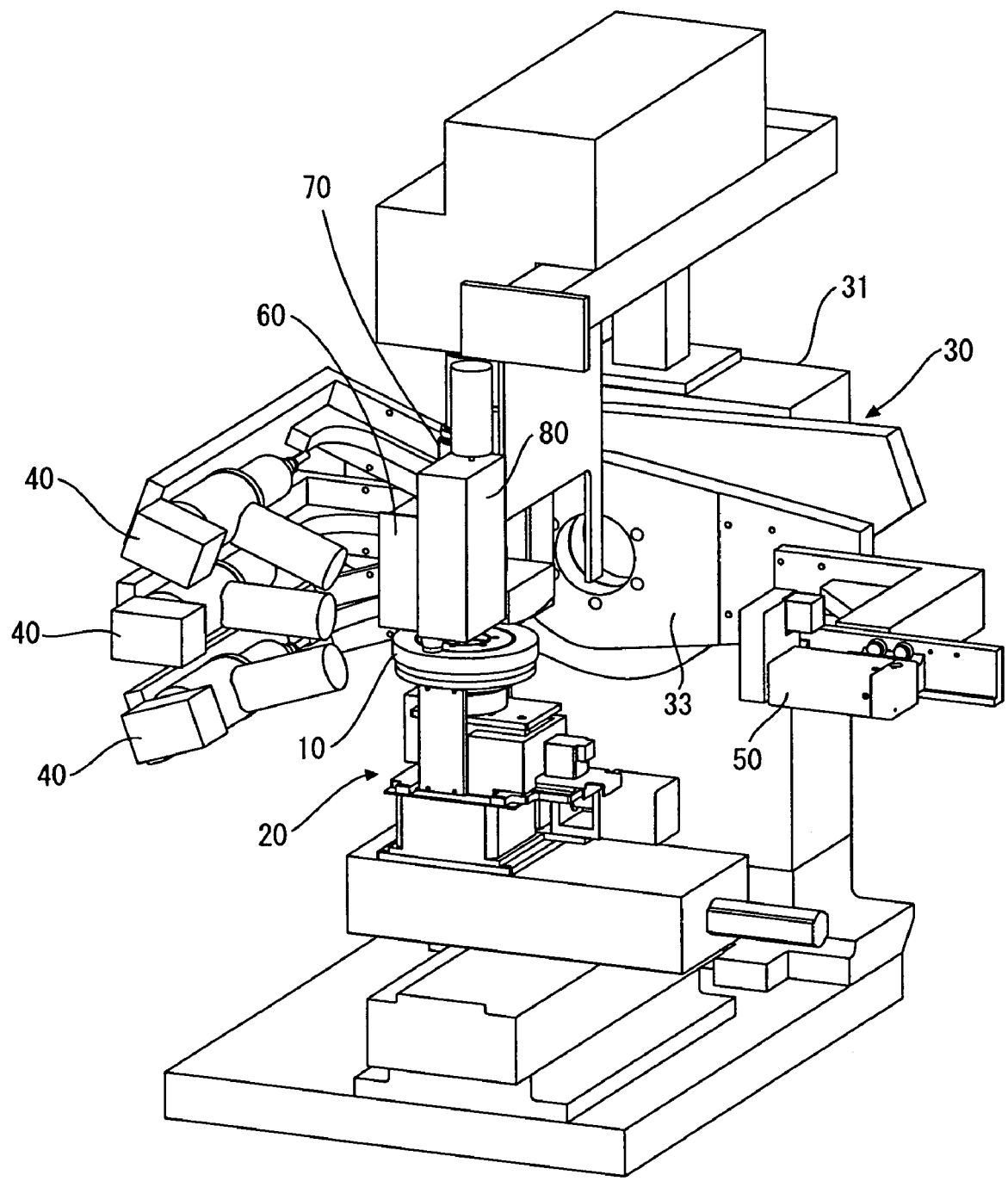
FIG. 2 is a perspective view showing the overall structure of the X-ray thin film inspection apparatus according to the embodiment of the present invention.
Figure 3:
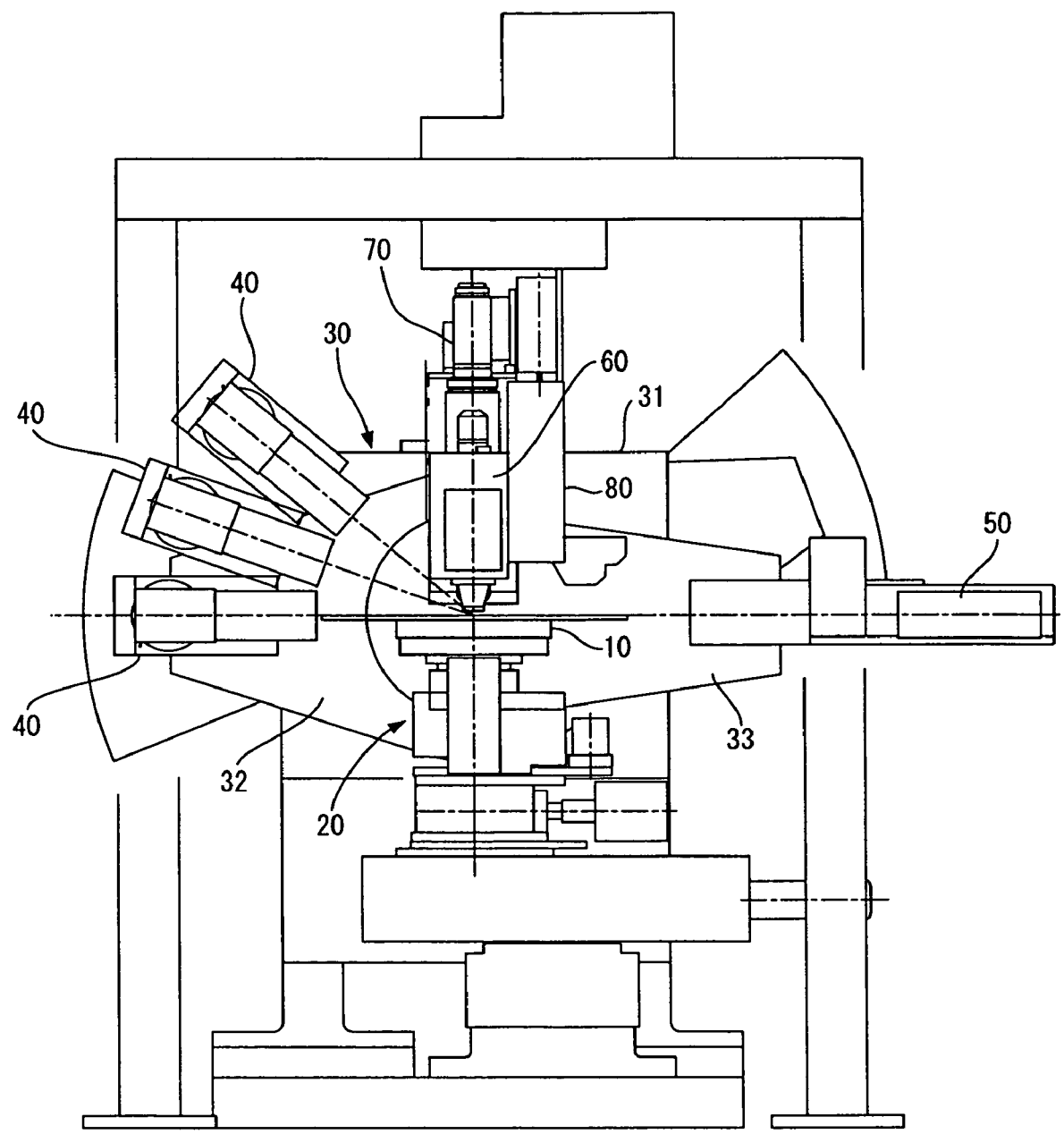
FIG. 3 is a front view showing the overall structure of the X-ray thin film inspection apparatus according to the embodiment of the present invention.
Figure 4:
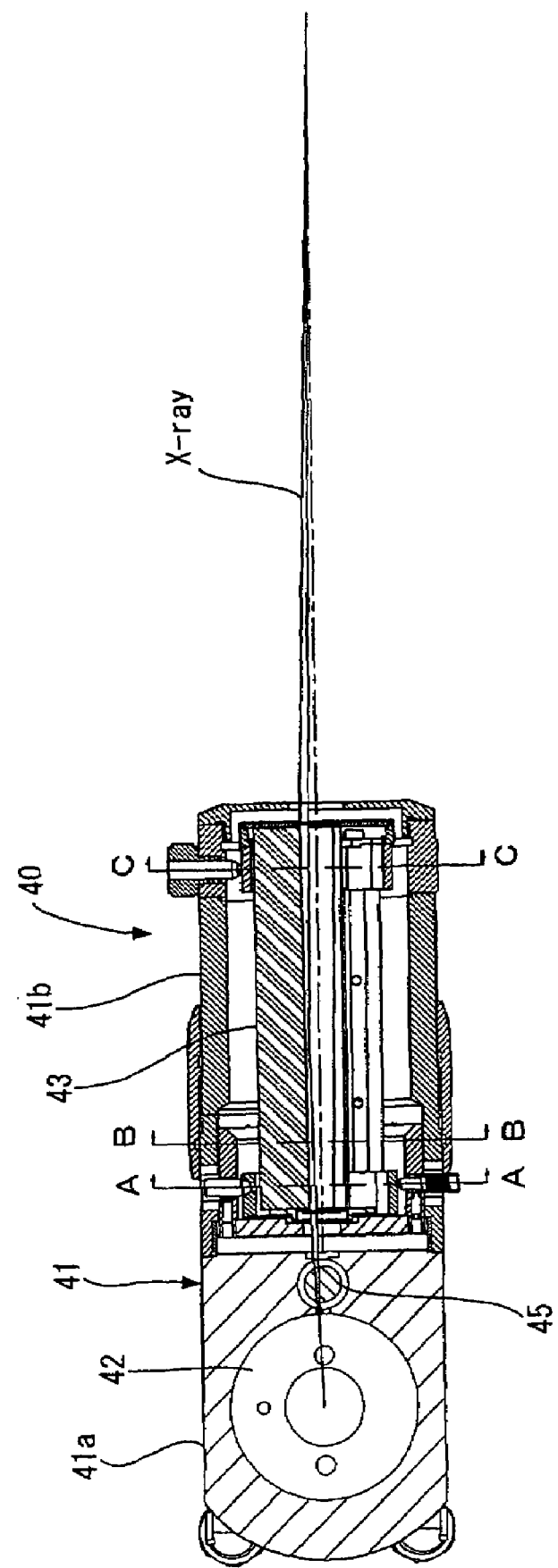
FIG. 4 is a front cross-sectional view showing an X-ray irradiation unit.
Figure 5A:
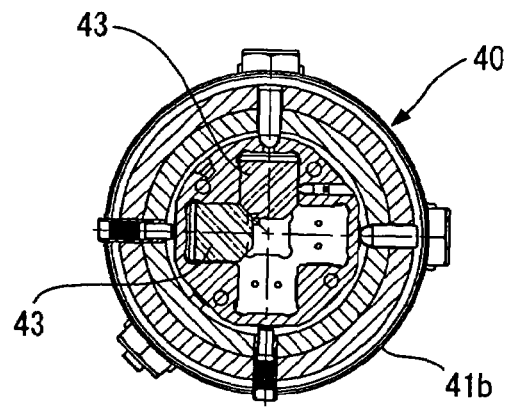
FIG. 5A is a cross-sectional view taken along A-A line of FIG. 4.
Figure 5B:
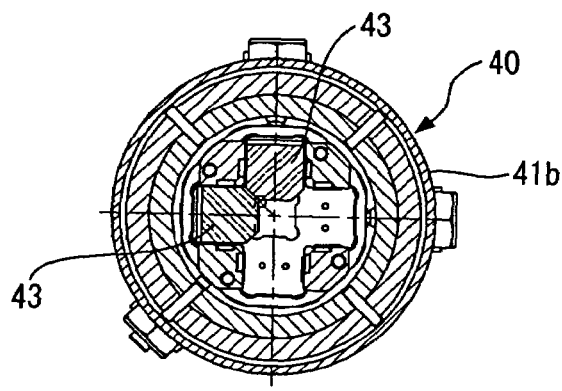
FIG. 5B is a cross-sectional view taken along B-B line of FIG. 4.
Figure 5C:
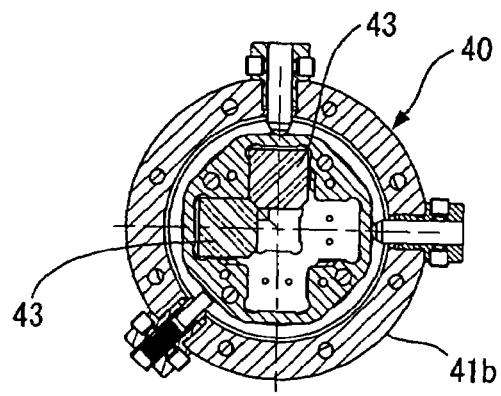
FIG. 5C is a cross-sectional view taken along C-C line of FIG. 4.

Construction of X-ray Thin Film Inspection Apparatus:

FIGS. 1 and 2 are perspective views achieved when the overall structure of the X-ray thin film inspection apparatus according to the embodiment is viewed from different visual fields, and FIG. 3 is a front view showing the X-ray thin film inspection apparatus.

The X-ray thin film inspection apparatus is equipped with a sample table 10, a positioning mechanism 20, a goniometer 30, an X-ray irradiation unit 40, an X-ray detector 50, a fluorescent X-ray detector 60, and an optical camera 70 comprising a CCD camera, etc.

The sample table 10 is constructed by a flat board on which a semiconductor wafer as an inspection target is disposed, and supported by the positioning mechanism 20.

The positioning mechanism 20 contains a horizontally moving mechanism freely movable in two perpendicular directions (X, Y directions) on any plane (horizontal plane or the like), an elevating mechanism freely movable in the vertical direction (Z direction) to the plane concerned and an in-plane rotating mechanism. The positioning mechanism 20 thus constructed moves the sample table 10 in the X, Y, Z directions and also rotated on the plane so that any measurement target portion on the semiconductor wafer disposed on the upper surface of the sample table 10 is positioned to a converged position of irradiated X-rays in a predetermined direction described later.

The goniometer 30 comprises a goniometer main body 31 and first and second swing arms (swing members) 32 and 33 mounted on the goniometer main body 31. The respective swing arms 32 and 33 are designed so as to be swung around the axis (θ axis) perpendicular to the sheet surface of FIG. 3 along a virtual plane perpendicular to the upper surface of the sample table (in parallel to the sheet surface of FIG. 3) in the same direction or in the opposite directions. That is, the swing arms 32 and 33 are swung on the virtual plane with the θ axis as a rotational center. Here, a plurality of (three in the figures) X-ray irradiation units 40 are mounted on the first swing arm 32 so as to be arranged in the swing direction. Furthermore, the X-ray detector 50 is mounted on the second swing arm 33.

The number of the X-ray irradiation units 40 mounted on the first swing arm 32 may be set to any number in conformity with the application. For example, one, two or four or more X-ray irradiation units 40 may be mounted on the first swing arm 32.

As shown in FIGS. 4, 5A to 5C, the X-ray irradiation unit 40 is designed to have a module structure having an X-ray tube 42 and an X-ray optical element 43 contained in a tube shield (unit main body) 41, thereby implementing a compact and light-weight design of the X-ray irradiation unit 40. The tube shield 41 is formed of metal material for shielding X-rays, and it is divided into a first tube 41a containing the X-ray tube 42 and a second tube 41b containing the X-ray optical element 43. The respective tubes 41a, 41b are joined to each other and unified into one body by a fastening member such as a bolt.

Figure 6:
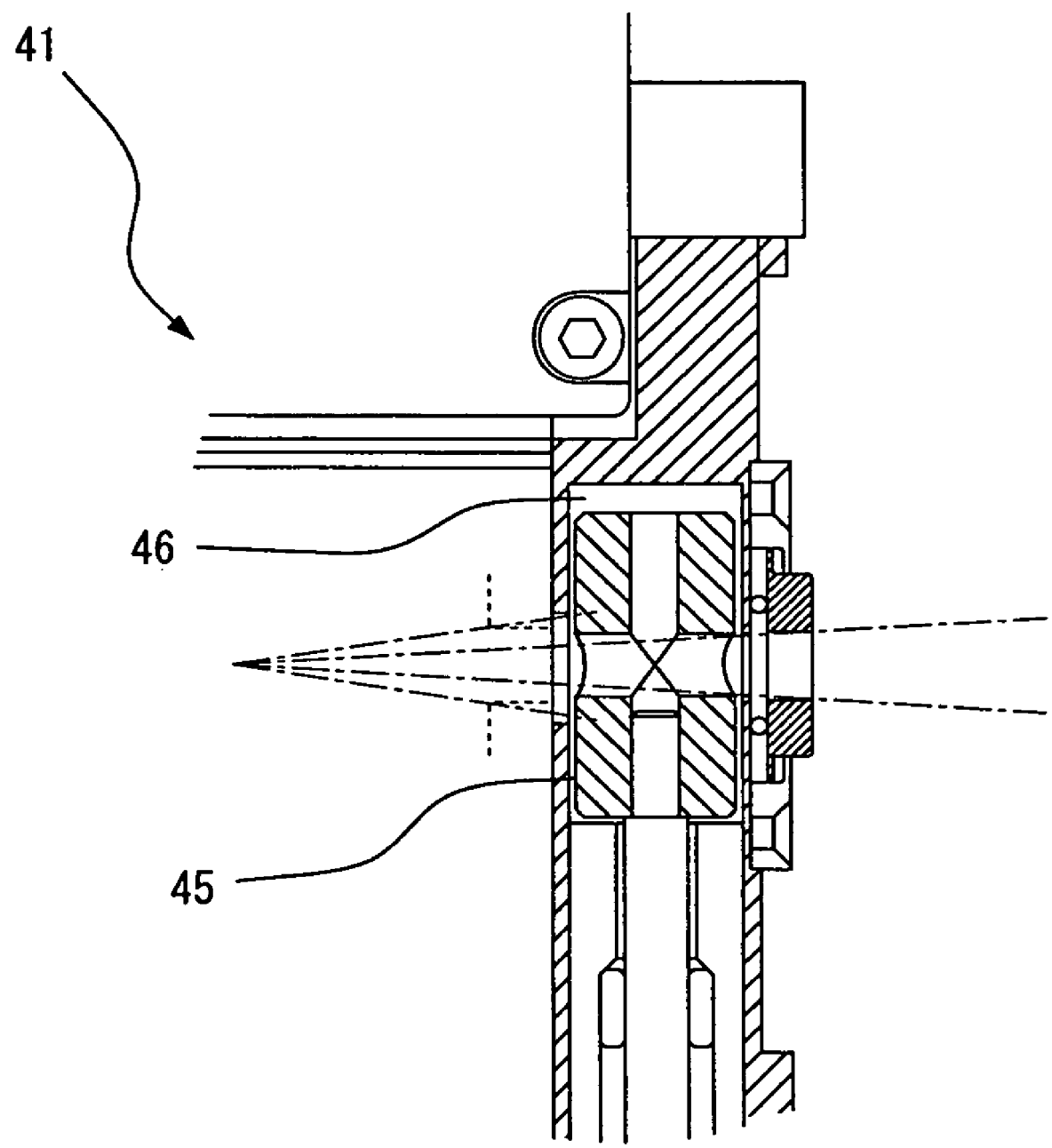
FIG. 6 is an enlarged cross-sectional view showing a shutter portion of the X-ray irradiation unit.

An X-ray passage for leading X-rays radiated from the X-ray tube 42 to the exit is formed in the tube shield 41, and a shutter 45 is provided at the intermediate portion of the X-ray passage. The shutter 45 is designed to be opened/closed through the rotation thereof. A fluid passage 46 is formed so as to surround the shutter 45 as shown in an enlarged view of FIG. 6. Gas such as air, nitrogen or argon gas is supplied from a gas supply source (not shown) into the fluid passage 46 and fluidized there in so that by-product materials such as $NO_x$ are prevented from adhering to the surface of the shutter 45, thereby preventing corrosion of the shutter 45.

For example, a micro focus X-ray tube having an electron beam focus size of about ϕ30 μm on a target and output power of about 25 W may be used as the X-ray tube 42. Copper (Cu), molybdenum (Mo) or the like may be selected as a target material as occasion demands. Other materials such as iron (Fe), cobalt (Co), tungsten (W), chromium (Cr) or silver (Ag) may be used. For example, plural X-ray irradiation units 40 equipped with x-ray tubes 42 containing different target materials may be mounted on the first swing arm 32.

Figure 7:
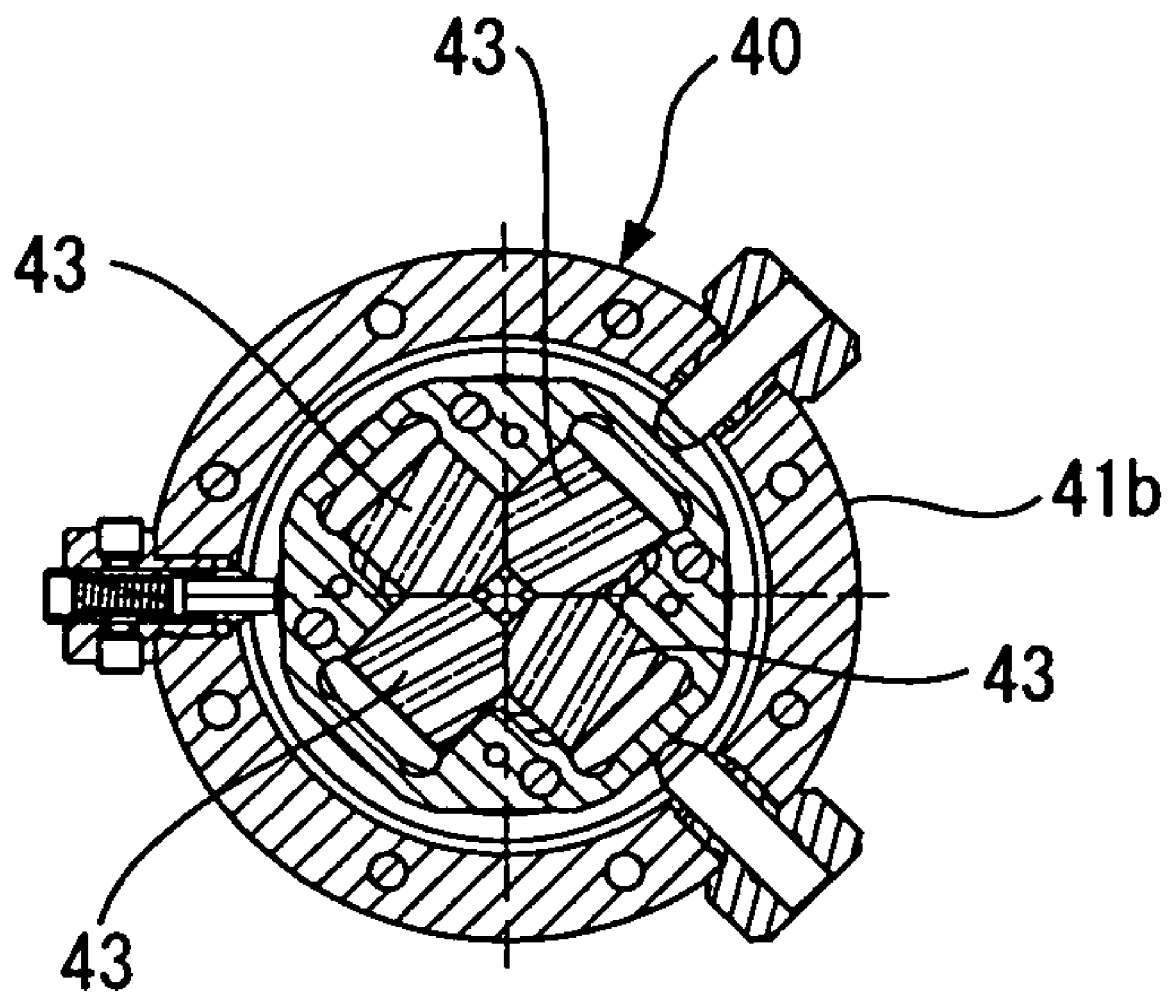
FIG. 7 is a cross-sectional view showing a modification of the X-ray irradiation unit in association with FIG. 5C.

A confocal mirror for converging X-rays generated from the X-ray tube 42 to a predetermined convergent position is used as the X-ray optical element 43. The confocal mirror is constructed by two or four multilayer film mirrors. FIGS. 4, 5A to 5C show a structure having two multilayer film mirrors, and FIG. 7 shows a structure having four multilayer film mirrors. The confocal mirror efficiently reflects and converges the X-rays generated from the X-ray tube 42, and monochronizes the X-rays. For example, when Cu target is used in the X-ray tube 42, X-rays are monochronized into CuKα, and when Mo target is used in the X-ray tube 42, X-rays are monochronized into MoKα. The multi-layer film mirror may be properly selected in accordance with the wavelength of the X-rays to be monochronized.

Here, the confocal mirror comprising the two multilayer film mirrors will be further described in detail with reference to FIGS. 8 and 9.

Figure 8:
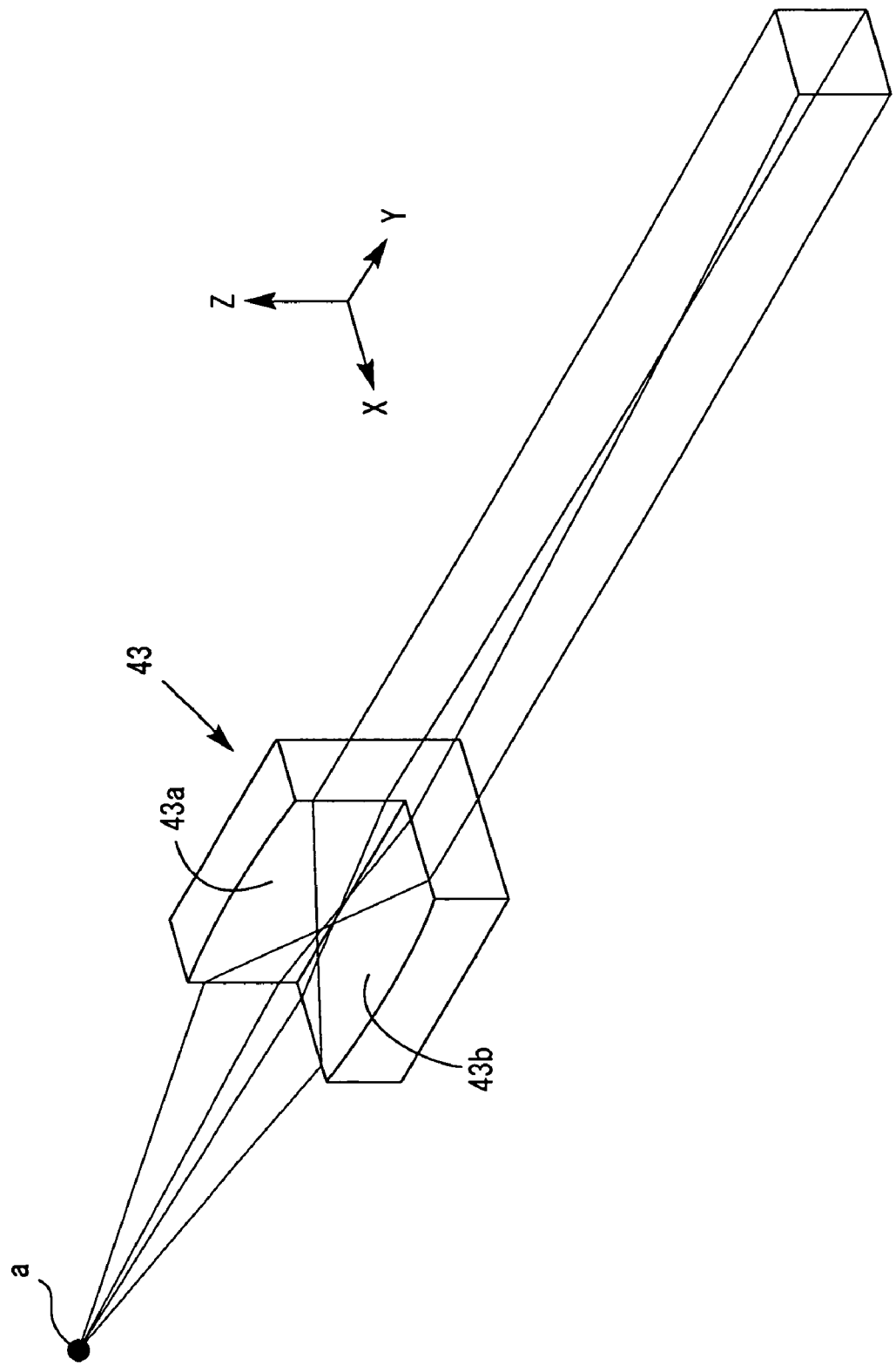
FIG. 8 is a perspective view showing the function of a confocal mirror.

The confocal mirror 43 shown in FIG. 8 is constructed by a first mirror having a first reflection face 43a and a second mirror having a second reflection face 43b. The first and second reflection faces 43a and 43b are formed of artificial multilayer films and designed in a paraboloid shape, and they are joined to each other so as to intersect to each other at about 90 degrees at the side edges thereof. That is, the confocal mirror 43 is a multilayer film mirror having a so-called side-by-side structure.

By using the confocal mirror 43 thus constructed, an X-ray beam emitted from the X-ray focal point a of the X-ray tube (which is a diverging beam) can be collimated on both the XY plane and the YZ plane. The X-rays which are first reflected from the first reflection face 43a are further reflected from the second reflection face 43b and go out of the confocal mirror 43. On the other hand, the X-rays which are first reflected from the second reflection face 43b are further reflected from the first reflection face 43a and go out of the confocal mirror 43. The first reflection face 43a serves to collimate the X-rays within the XY plane, and the second reflection face 43b serves to collimate the X-rays within the YZ plane.

Since the X-ray beam diverging from the X-ray focal point a is collected by the paraboloids to be collimated, a collimated beam having high luminance can be achieved. By using the confocal mirror 43 and the micro focus X-ray tube as described above, the cross-sectional shape of the incident X-ray beam just before the X-ray beam is incident to a sample is equal to 1 mm×0.1 mm, for example. The divergence angle of the X-ray beam on the XY plane and the YZ plane is equal to 0.03 degree or less.

Figure 9:
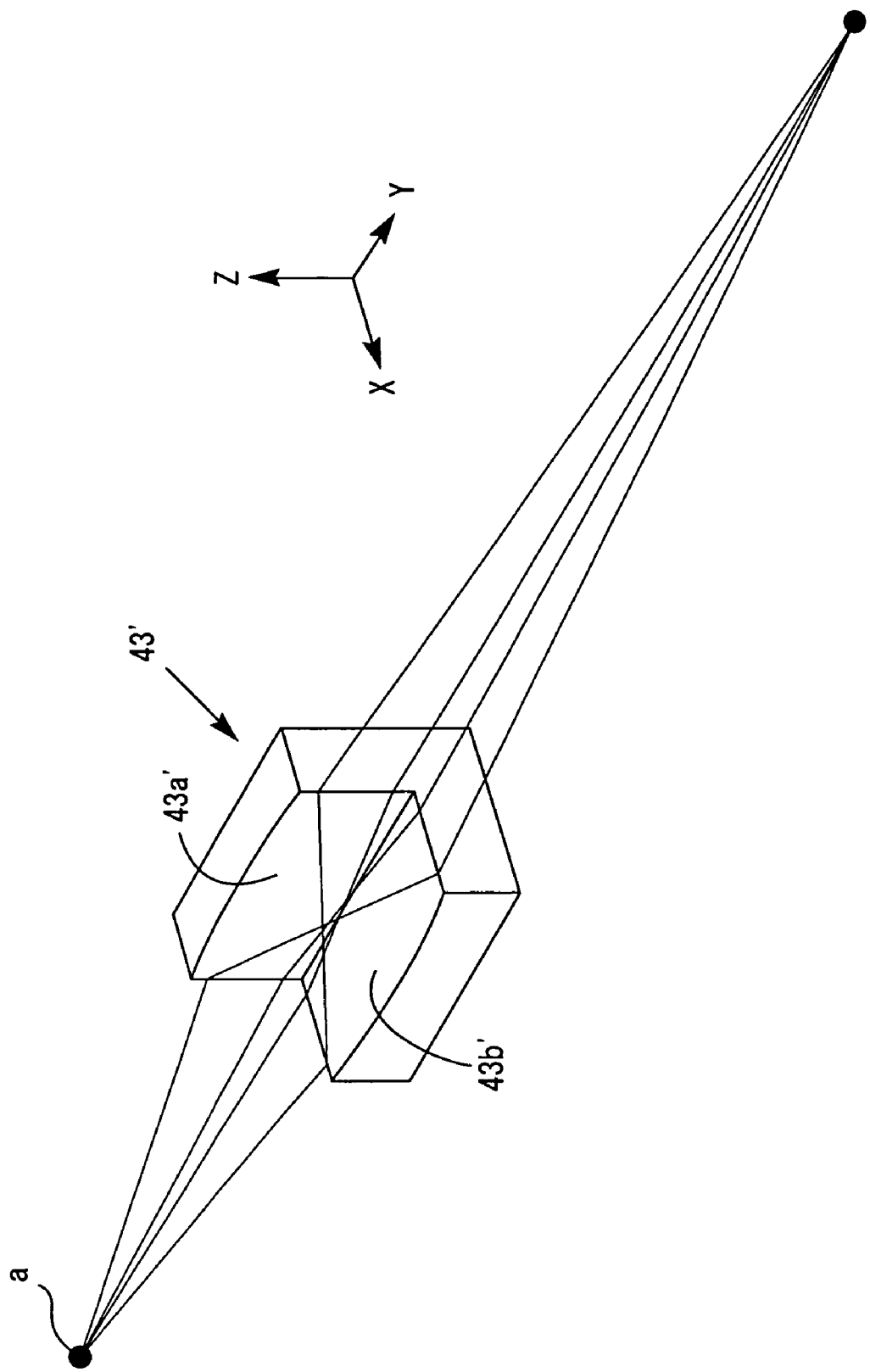
FIG. 9 is a perspective view showing the function of a confocal mirror having another structure.

A confocal mirror 43' shown in FIG. 9 comprises two reflection faces 43a' and 43b' that are designed to have an elliptic arc face shape. This construction makes an X-ray beam a converged beam which is converged onto the surface of the sample within the XY plane and the YZ plane. The confocal mirror of FIG. 9 causes a larger divergence angle, but provides high incidence X-ray intensity as compared with the confocal mirror shown in FIG. 8. By using the confocal mirror 43' and the micro focus X-ray tube described above, the cross-sectional shape of the incident X-ray beam just before the X-ray is incident to the sample is equal to 0.05 mm×0.05 mm, for example. At this time, assuming that the overall multilayer film mirror is used, the divergence angle is increased to about one degree. However, when the divergence angle is restricted by a slit to collimate the X-ray beam within the XY plane, the divergence angle can be set to about 0.05 degree to measure reflectivity.

When the X-ray irradiation unit 40 is designed as described above, X-rays having strong intensities of $10^7$ cps (counts per second) or more can be converged onto a minute focal point of about φ100 μm by using a micro focus X-ray tube having an electron beam focal point size of about φ30 μm on a target and output power of about 25 W.

The convergence position of the X-rays is set to be coincident with the measurement position, and any measurement target site in the semiconductor wafer is positioned to the convergence position concerned by the positioning mechanism 20. The measurement position is set on the θ-axis of the goniometer 30.

As shown in FIGS. 1 to 3, plural (three in the figures) X-ray irradiation units 40 are mounted on the first swing arm 32 so as to be arranged in the swing direction, whereby any one of the plural X-ray irradiation units 40 can be selected and the selected X-ray irradiation unit 40 can be positioned at any angle with respect to the measurement position with high precision. That is, the X-rays can be irradiated to the measurement position at any irradiation angle with high precision.

For example, when X-ray reflectivity is measured by this apparatus, one of the X-ray irradiation units 40 which generates desired X-rays is selected, and the selected X-ray irradiation unit 40 is disposed so that the X-rays are irradiated at a low angle at which the X-rays are very close to the surface of the semiconductor wafer serving as a measurement target. When a normal X-ray diffraction measurement is carried out, the position of the selected X-ray irradiation unit 40 is successively moved to properly change the incident angle of the X-rays to the semiconductor wafer. Furthermore, as described later, when aluminum thin film is set as a measurement target and a fluorescent X-ray measurement is carried out on the aluminum thin film, the selected X-ray irradiation unit 40 is disposed so that X-rays are irradiated to the measurement target at a low angle.

According to the X-ray thin film inspection apparatus of this embodiment, the selection of one of these X-ray irradiation units 40 and the positioning of the X-ray irradiation unit 40 thus selected can be performed with high precision by merely swinging the first swing arm 32.

Furthermore, according to the construction that the X-ray irradiation unit(s) 40 is mounted on the first swing arm 32, an angle scanning measurement can be performed in the X-ray reflectivity measurement by merely swinging the first swing arm 32. Here, JP-T-2003-529047 discloses an example of measuring the reflection angle over several angles by using a curved crystal spectroscope. According to this method, scattered X-rays other than the reflection X-rays enter the X-ray detector, and thus the quality of measurement data is degraded, so that it is particularly difficult to measure thin film.

On the other hand, according to the X-ray thin film inspection apparatus of this embodiment, the X-ray reflectivity measurement based on the angle scanning measurement can be performed, so that the incidence of the scattered X-rays to the X-ray detector 50 can be suppressed and thus measurement data can be achieved with high precision.

The X-ray detector 50 is used for the X-ray reflectivity measurement (XRR) and the X-ray diffraction measurement (XRD), and the fluorescent X-ray detector 60 is used for the fluorescent X-ray measurement (XRF). According to the X-ray reflectivity measurement, the interference between reflected X-rays at the film surface and reflected X-rays at the interface between the film and the substrate is measured to determine the film thickness and the density, and thus the measurement precision of angstrom order is achieved for the film thickness. Furthermore, according to the fluorescent X-ray measurement, the measurement of wire film having a relatively large thickness can be performed with high precision. The X-ray thin film inspection apparatus of this embodiment can carry out not only the X-ray reflectivity measurement and the fluorescent X-ray measurement, but also the X-ray diffraction measurement as occasion demands.

It is preferable that an avalanche photodiode (APD) having a broad dynamic range for incident X-rays is used as the X-ray detector 50. In the case where APD is used as the X-ray detector 50, even when X-rays having strong intensities are incident, there is not needed any means for attenuating the X-ray intensities such as an attenuator because APD has a broad detection dynamic range (for example, APD can measure the X-ray intensity of 10,000,000 counts or more per second), and thus the measurement time can be greatly shortened.

As described above, when APD is used as the X-ray detector 50, it is unnecessary that an attenuator or the like is inserted to attenuate X-rays and then the measurement is carried out, so that the time needed to achieve data can be shortened and the measurement can be completed in the same level of time as the inspection method using a one-dimensional array detector.

Figure 10:
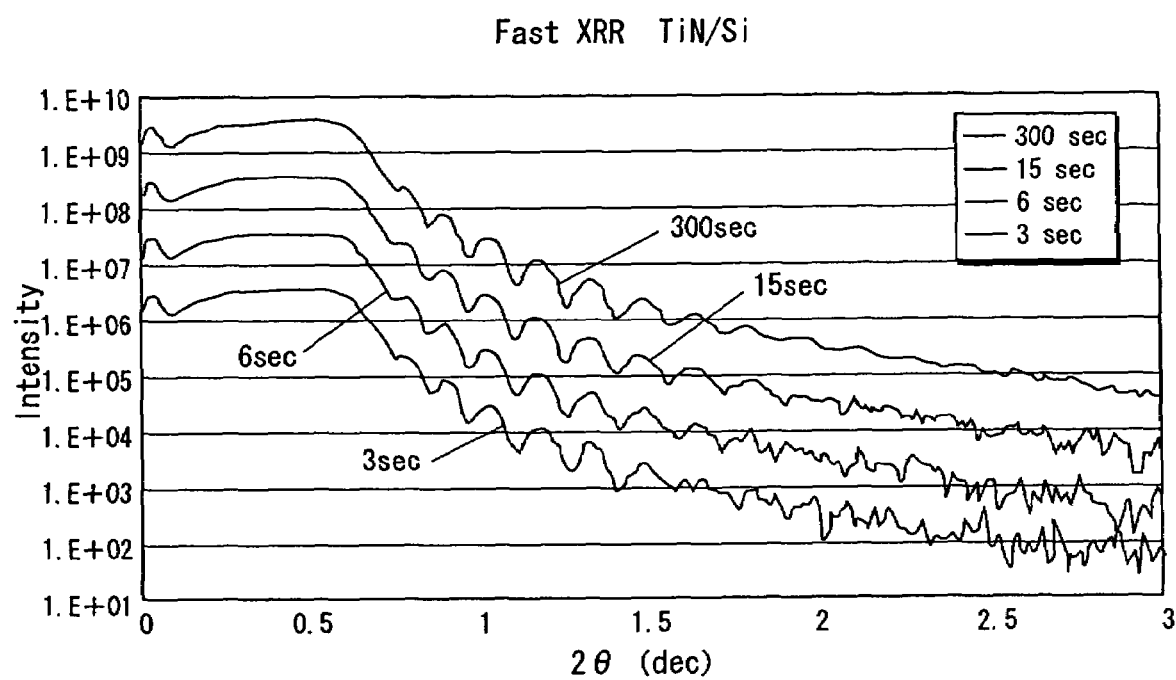
FIG. 10 is a graph showing XRR measurements over 2θ-value from 0 to 3 degrees when the inspection apparatus of the present invention is used and the measurement time is varied.

FIG. 10 shows a graph showing measurement results achieved when APD is used, and specifically FIG. 10 shows measurement results when the X-ray irradiation unit 40 is scanned over the angle range from 0 degree to 3 degrees (2θ) in 300 seconds, 15 seconds, 6 seconds and 3 seconds (i.e., the scanning speed is set to 300 seconds, 15 seconds, 6 seconds and 3 seconds over the angle range from 0 degree to 3 degrees). Furthermore, FIG. 11 is a table showing analysis results achieved by using the data of FIG. 10. It is understood from FIGS. 10 and 11 that sufficient inspection can be performed by even the measurement of 3 seconds.

Here, the counting rate of the X-ray detector and the dynamic range under measurement will be described.

Figure 12:
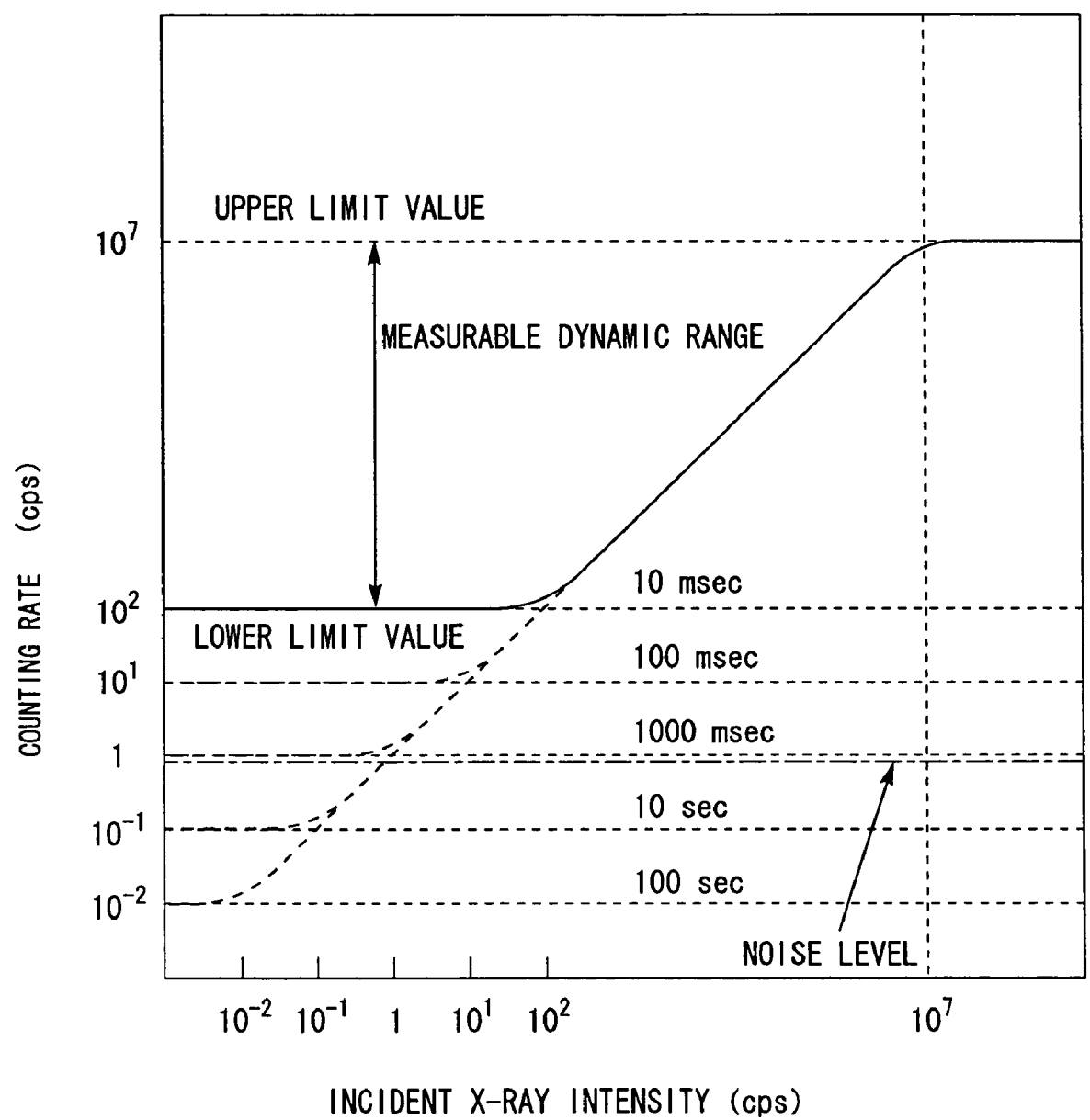
FIG. 12 is a graph showing a dynamic range of the X-ray detector.

FIG. 12 is a graph showing a graph showing the relationship between the intensity of X-rays (unit is cps) incident to the X-ray detector and the counting rate (unit is cps) corresponding to the output of the X-ray detector.

As the incident X-ray intensity is very large, the counting rate is saturated. At this time, the saturated counting rate corresponds to the measurable upper limit counting rate. In FIG. 12, this value is indicated by "upper limit value", and in this example, it is equal to $10^7$ cps.

On the other hand, as the incident X-ray intensity is very small, the measurement is impossible. There are two factors for determining the lower limit value. A first factor is a measurement time per point (position), and a second factor is a noise level of the X-ray detector.

First, the first factor will be described.

When the measurement time per point is very short, for example, it is equal to 10 msec, in order to count at least one X-ray photon, the X-ray intensity of 1 count/10 msec=100 cps is needed. When the X-ray intensity is lower than this count value, there occurs any one of the situation that one X-ray photon is counted for the measurement time and the situation that no X-ray photon is counted for the measurement time, however, in both the situations, it is impossible to specify the actual X-ray intensity.

Accordingly, it is impossible to achieve any measurement result less than 100 cps from the X-ray detector. In this sense, this measurement limit is represented by a horizontal line of 10 msec in FIG. 12. At this time, the lower limit value of the counting rate is equal to 100 cps. Likewise, when the measurement time per point is equal to 100 msec, the lower limit counting rate is equal to 10 cps, and when the measurement time per point is equal to 1000 msec (1 second), the lower limit counting rate is equal to 1 cps.

Next, the second factor will be described.

The X-ray detector has an intrinsic noise level, and the incident X-ray intensity lower than the intrinsic noise level is hidden in the noise level and thus undetectable. In the graph of FIG. 12, the noise level is equal to about 1 cps, and it is impossible to detect any incident X-ray intensity lower than this value. As a result, larger one of the counting rate corresponding to the noise level and the lower limit counting rate determined by the measurement time per point corresponds to the lower limit counting rate under the measurement concerned. This will be described with reference to the graph of FIG. 12. That is, when the measurement time per point is equal to 1000 msec or less, the lower limit counting rate determined by the measurement time per point corresponds to the lower limit counting rate under the measurement concerned. Conversely, when the measurement time per point exceeds 1000 msec, the noise level contributes to the lower limit counting rate, and the lower limit counting rate is independent of the measurement time. In the graph of FIG. 12, a solid line represents a counting rate when the measurement time per point is equal to 10 msec. At this time, the upper limit value is equal to $10^7$ cps, the lower limit value is equal to 100 cps, and the measurable dynamic range of five digits can be secured.

Figure 13:
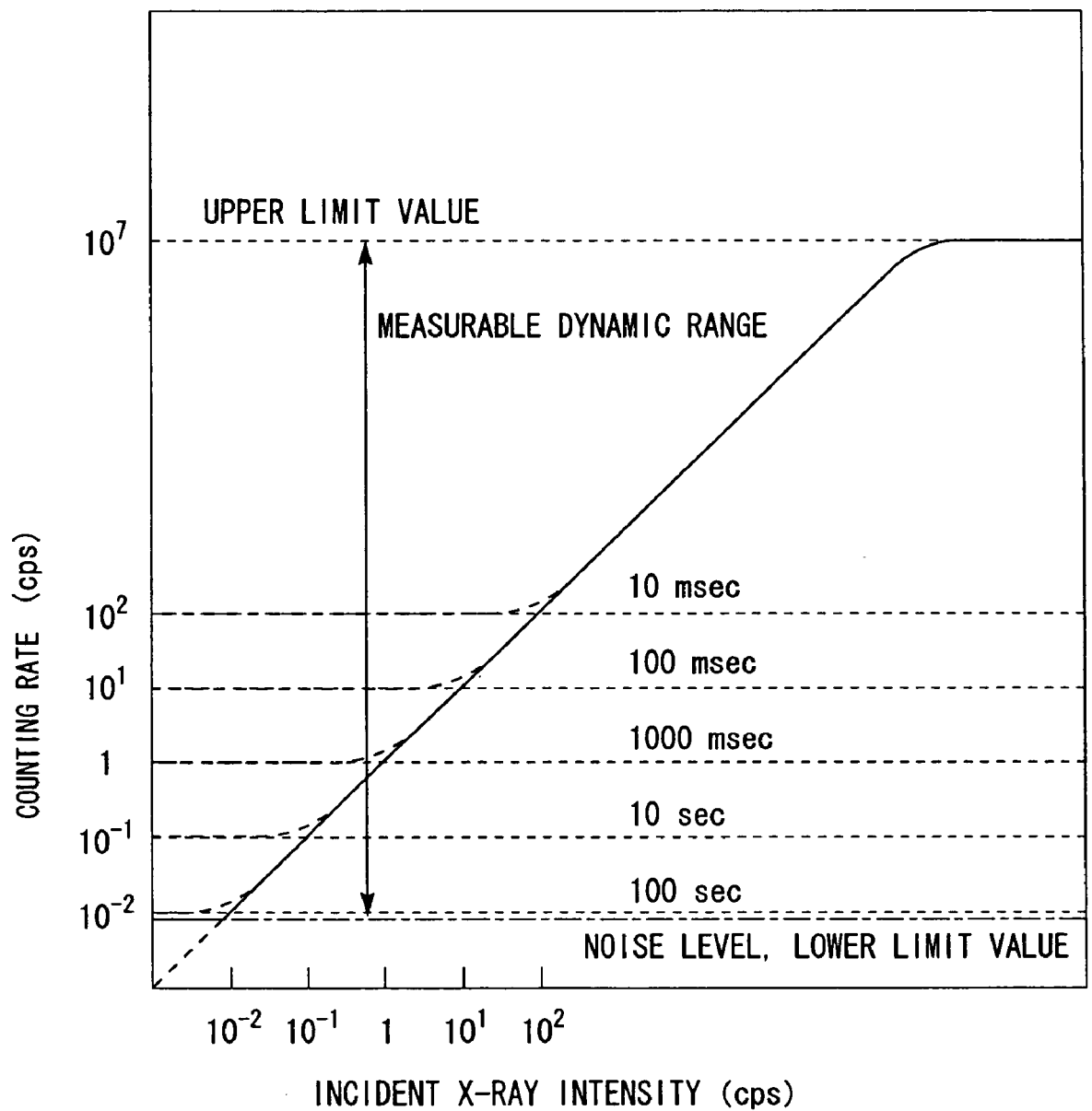
FIG. 13 is another graph showing a dynamic range of the X-ray detector.

FIG. 13 is a graph in the case of use of an X-ray detector in which the noise level is very low (about 0.01 cps), which corresponds to the graph of FIG. 12. In this case, even when the measurement time per point is greatly lengthened, the lower limit counting rate caused by the increase of the measurement time is never reduced to less than the noise level. A solid line of FIG. 10 represents the counting rate when the measurement time per point is equal to 100 seconds or more. When the measurement time per point is equal to 100 seconds, the lower limit counting rate is equal to 0.01 cps. That is, at this time, the lower limit counting rate is finally equal to the noise level. As described above, when the X-ray detector having a low noise level is used, the lower limit counting rate can be reduced to a very low value by lengthening the measurement time per point, whereby the dynamic range can be increased to a very large value. In the case of FIG. 13, the upper limit counting rate is equal to $10^7$ cps, the lower limit counting rate is equal to 0.01 cps, and thus the measurable dynamic range is equal to $10^9$.

APD has the upper limit counting rate of $10^8$ cps and the noise level of 0.002 cps. Accordingly, when APD is used, the time needed for the reflectivity measurement can be shortened to about several seconds, and the reflectivity curved line can be measured with a very large dynamic range by lengthening the measurement time per point.

Returning to FIGS. 1 to 3, an equipment exchange mechanism 80 is provided at the upper side of the sample table 10. The equipment exchange mechanism 80 is disposed to select one of the fluorescent X-ray detector 60 and the optical camera 70 and dispose the selected part (the fluorescent X-ray detector 60 or the optical camera 70) so that the selected part faces the convergence position (measurement position) of incident X-rays.

Figure 14:
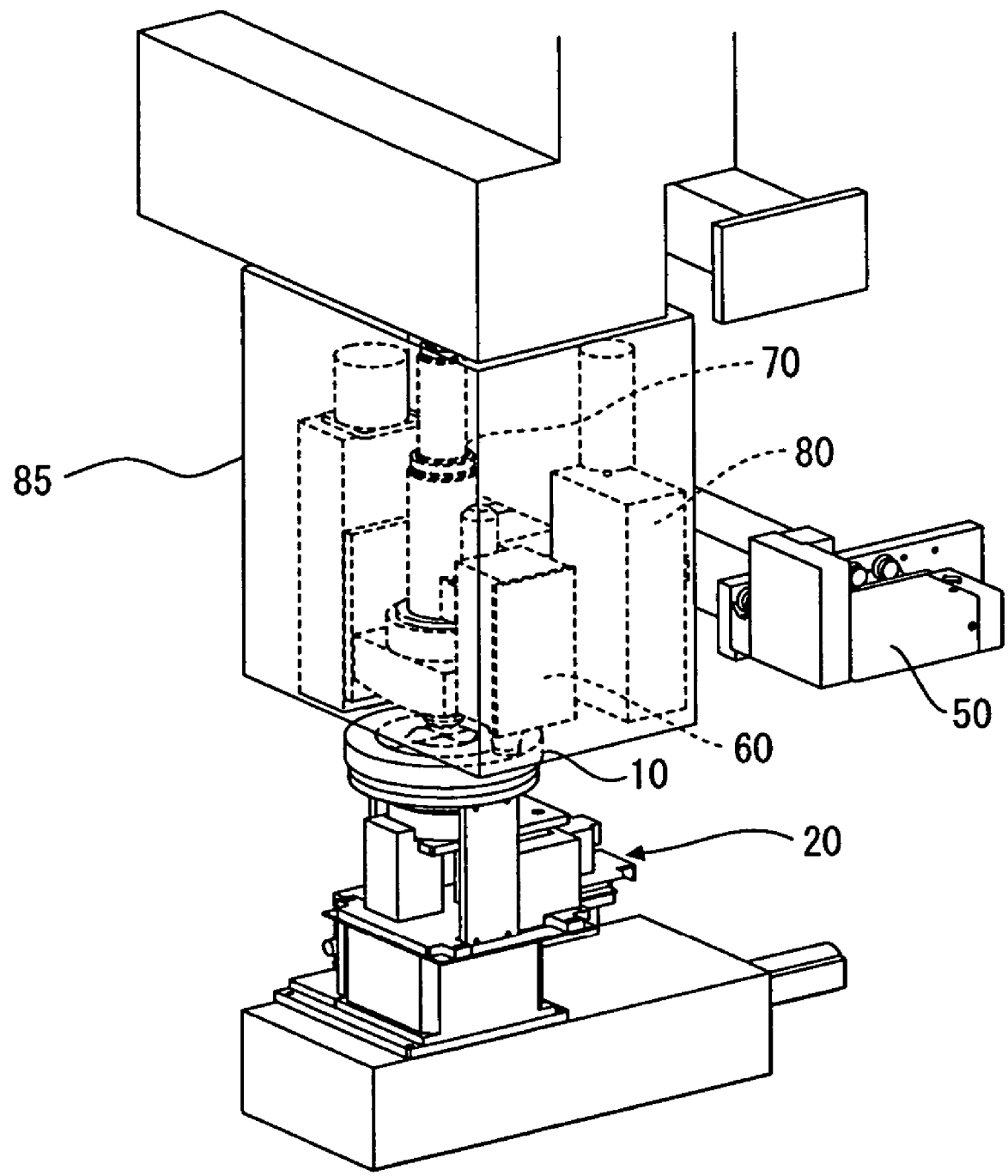
FIG. 14 is an enlarged perspective view showing the structure of a cover provided above a sample table.

The constituent elements located above the sample table 10 are covered by a cover 85 as shown in FIG. 14, whereby dust which may occur at the equipment exchange time can be prevented from falling onto the inspection target disposed on the sample table 10. A transmissible window for opening the visual field of the optical camera 70 is formed at the bottom surface of the optical camera 70. Furthermore, the inside of the cover 85 is exhausted by an exhausting device (not shown), whereby dust can be prevented from falling from the window.

The optical camera 70 is adjusted in advance so that the focal point thereof is coincident with the convergent position of the incident X-rays (that is, the measurement position). The image of the semiconductor wafer disposed on the sample table 10 is picked up by the optical camera 70, and subjected to pattern recognition by a pattern recognition circuit described later. The driving of the positioning mechanism 20 is controlled on the basis of the pattern recognition result of the pattern recognition circuit, whereby any measurement target site of the semiconductor wafer can be accurately positioned to the convergent position of the incident X-rays (measurement position) Here, since the mechanism for elevating the positioning mechanism 20 (i.e., moving the positioning mechanism 20 upwardly and downwardly) to make the measurement target site of the semiconductor wafer coincident with the focal point of the optical camera 70 is operated, the positioning operation in the height direction and the pattern recognition processing can be simultaneously performed, and thus the operation time can be greatly shortened.

Figure 15:
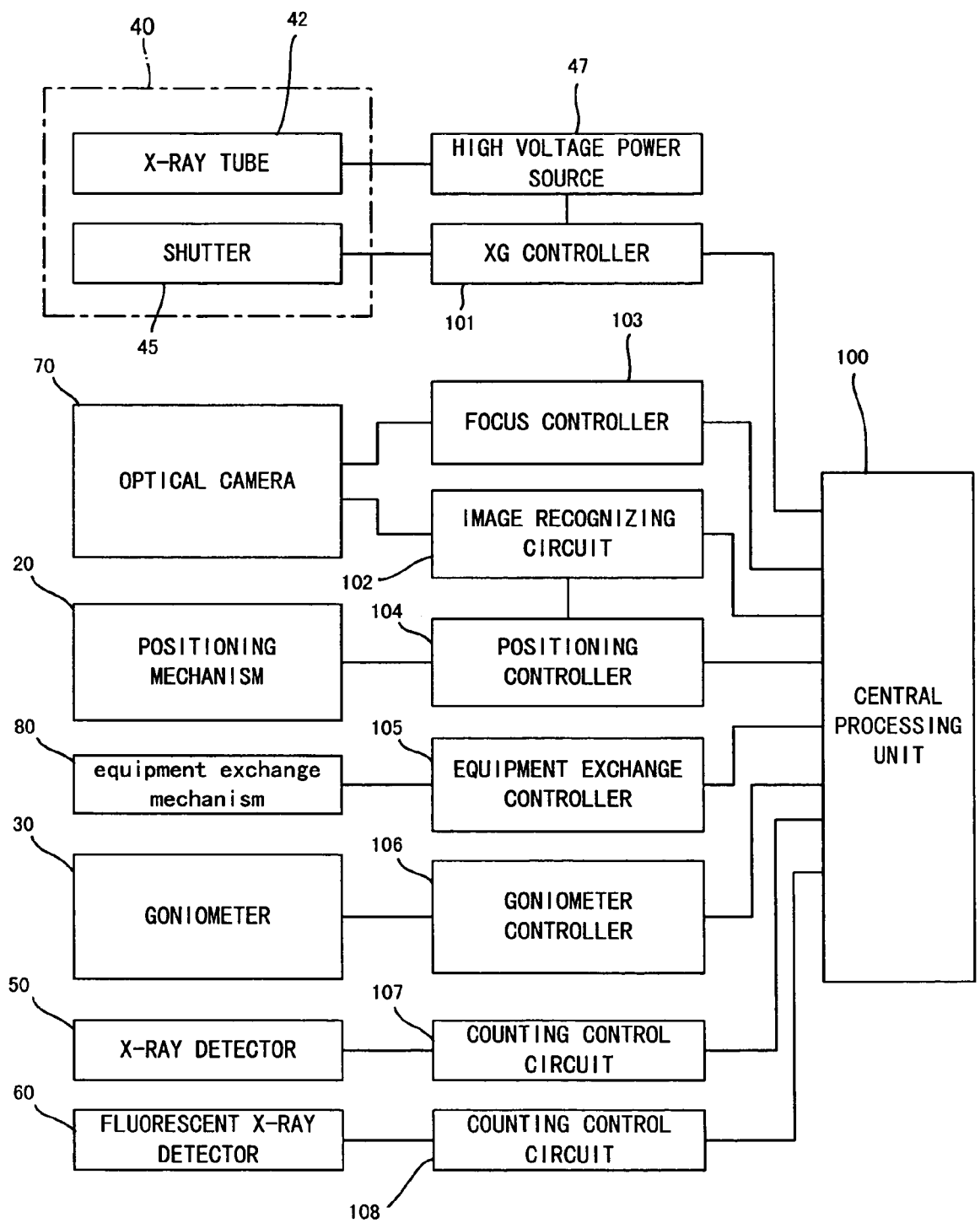
FIG. 15 is a block diagram showing a control system of the X-ray inspection apparatus according to the embodiment of the present invention.

FIG. 15 is a block diagram showing a control system for the X-ray thin film inspection apparatus according to this embodiment.

The voltage supply operation of a high voltage from a high voltage source 47 to the X-ray tube 42 installed in the X-ray irradiation unit 40 and the opening/closing operation of the shutter 45 are carried out by an XG controller 101. Furthermore, the image picked up by the optical camera 70 is subjected to pattern recognition in the pattern recognition circuit 102. The focal distance of the optical camera 70 is adjusted by a focus controller 103. As described above, the focal point of the optical camera 70 is set to be coincident with the convergent position of the incident X-rays (that is, the measurement position). A positioning controller 104 controls the driving of the positioning mechanism 20 on the basis of the pattern recognition result of the pattern recognizing circuit 102. The equipment exchange mechanism 80 is controlled by an equipment exchange controller 105, and the goniometer 30 is controlled by a goniometer controller 106.

The XG controller 101, the pattern recognition circuit 102, the focus controller 103, the positioning controller 104, the equipment exchange controller 105 and the goniometer controller 106 are operated on the basis of set information from a central processing unit (CPU) 100. Furthermore, the X-ray detector 50 and the fluorescent X-ray detector 60 are controlled by counting control circuits 107 and 108, respectively. These controllers, CPU and the count control circuits constitute the controller of the X-ray thin film inspection apparatus.

Figure 16:
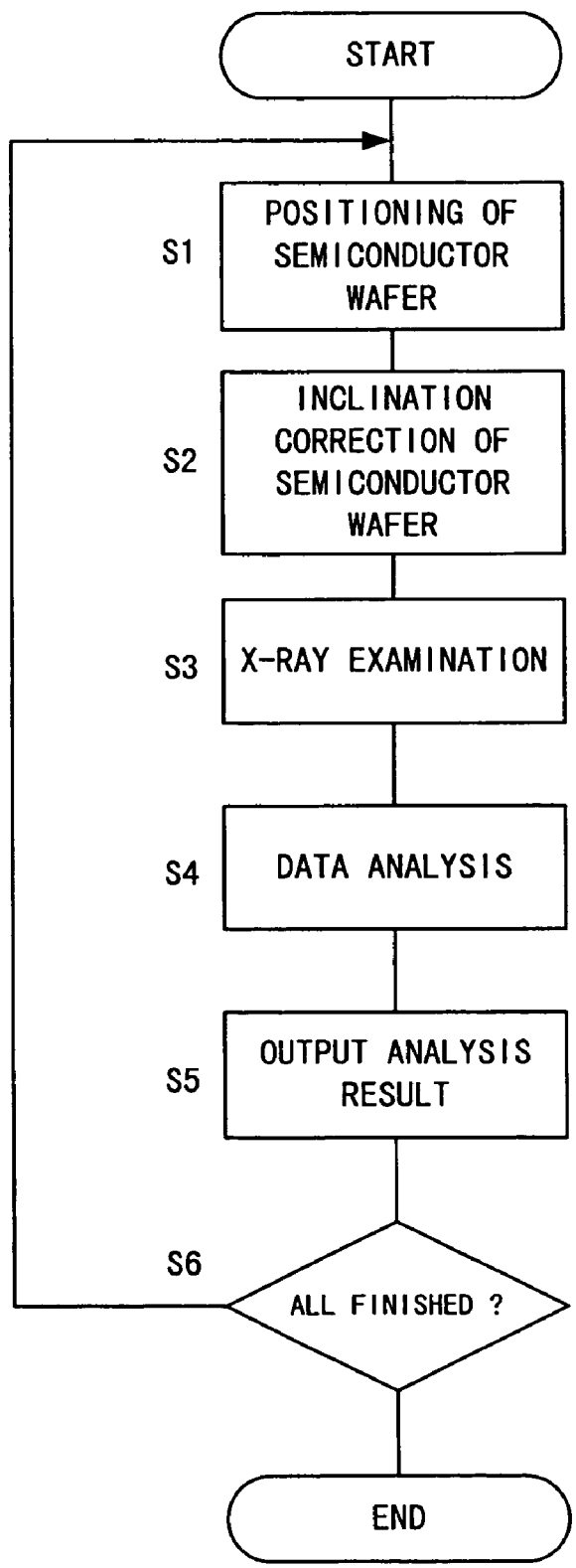
FIG. 16 is a control flowchart showing the X-ray inspection apparatus according to the embodiment of the present invention.

FIG. 16 is a control flowchart when the X-ray thin film inspection is carried out.

After a semiconductor wafer serving as an inspection target is disposed on the sample table 10, the measurement target site of the semiconductor wafer is positioned to the measurement position (step S1). The positioning is carried out by controlling the driving of the positioning mechanism 20. That is, the optical camera 70 picks up the image of the semiconductor wafer on the sample table 10, the pattern recognition circuit 102 carries out the pattern recognition on the image and the positioning controller 104 controls the driving of the positioning mechanism 20 on the basis of the recognition result. The positioning mechanism 20 is moved in the horizontal two directions (X-Y directions) and the height direction (Z direction) to dispose the measurement target site of the semiconductor wafer to the measurement position.

When a minute thin film pattern in a semiconductor device formed on the semiconductor wafer is set as a measurement target site, minute patterns of specific sites such as a scribe line, a memory portion, a dummy pattern and IC chip are beforehand stored in a storage unit such as a memory or the like provided to the pattern recognition circuit 102. When an inspection is carried out, an inspection target area of the semiconductor wafer serving as the inspection target is observed by using the optical camera 70, and the observed image and the minute pattern stored in advance are compared with each other, whereby the pattern recognition circuit 102 judges whether the inspection target area is the minute patter of the measurement target site. On the basis of the judgment result, the minute patter corresponding to the measurement target site is positioned to the measurement position by the positioning mechanism 20.

Furthermore, when a minute thin film pattern in a semiconductor device formed on the semiconductor wafer is set as a measurement target site as described above, it is preferable to dispose the minute pattern so that the longitudinal direction of the minute pattern is coincident with the incident direction of X-rays. This direction-matching operation can be performed through a short-distance movement by the movement in the horizontal two directions (X, Y directions) and the in-plane rotational movement of the positioning mechanism 20. This will be described with reference to FIG. 17.

Figure 17:
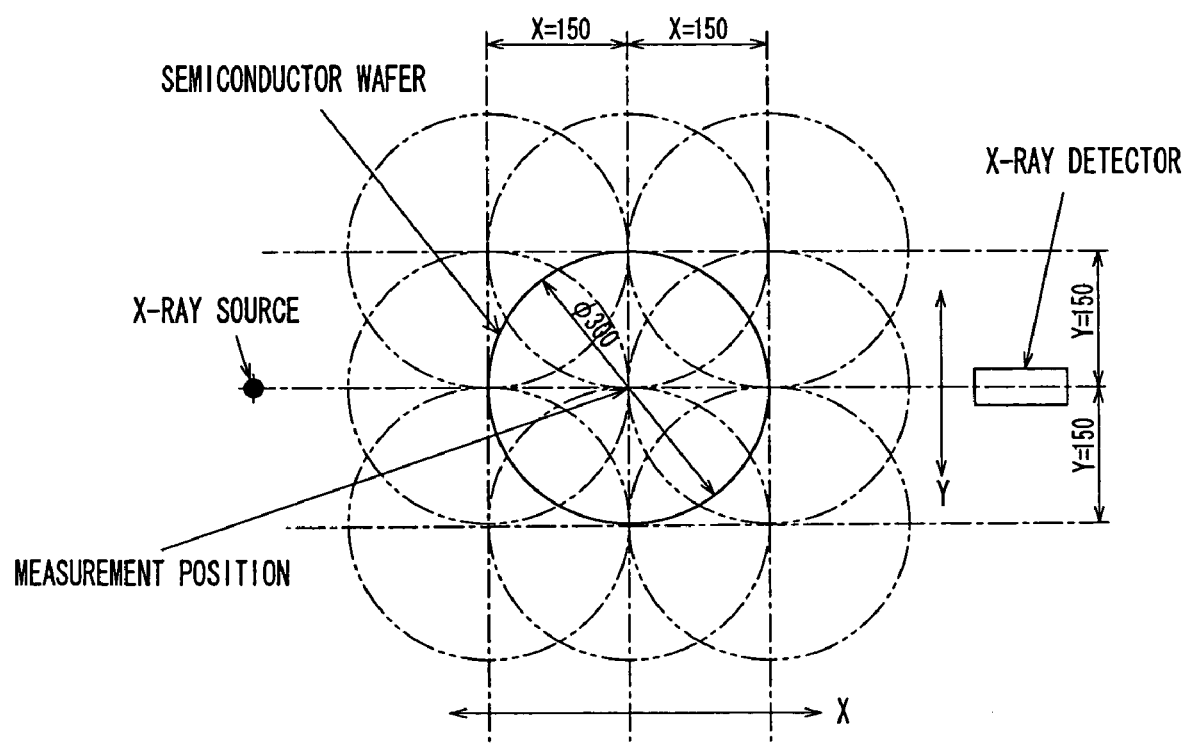
FIG. 17 is a comparison diagram showing a positioning operation of a semiconductor wafer.

As shown in FIG. 17, when the positioning operation and the direction-matching operation are carried out by only the movements in the horizontal two directions (X,Y directions), in order to set all the measurement target sites existing in the whole area of the semiconductor wafer to the measurement position, the movement distance corresponding to the diameter of the semiconductor wafer must be secured in each of the X and Y directions. Therefore, the peripheral structure of the sample table 10 is increased in size.

Figure 18:
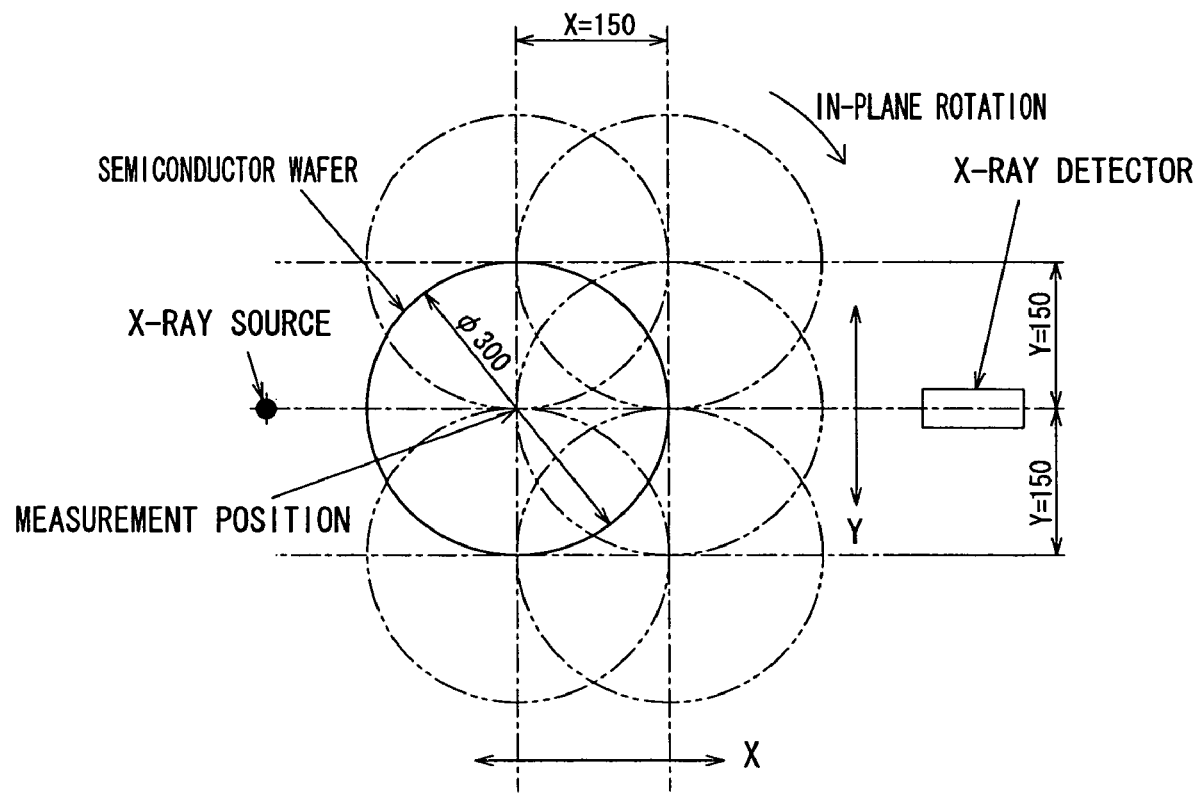
FIG. 18 is a diagram showing the positioning operation of the semiconductor wafer.

In this embodiment, as shown in FIG. 18, the positioning operation and the direction-matching operation are carried out by the movement of the horizontal two directions (X, Y-directions) and the in-plane rotational movement, and thus the movement distance corresponding to a half of the diameter of the semiconductor wafer may be secured for the movements in the X-direction and the Y-direction, so that the peripheral structure of the sample table 10 can be miniaturized.

Figure 19:
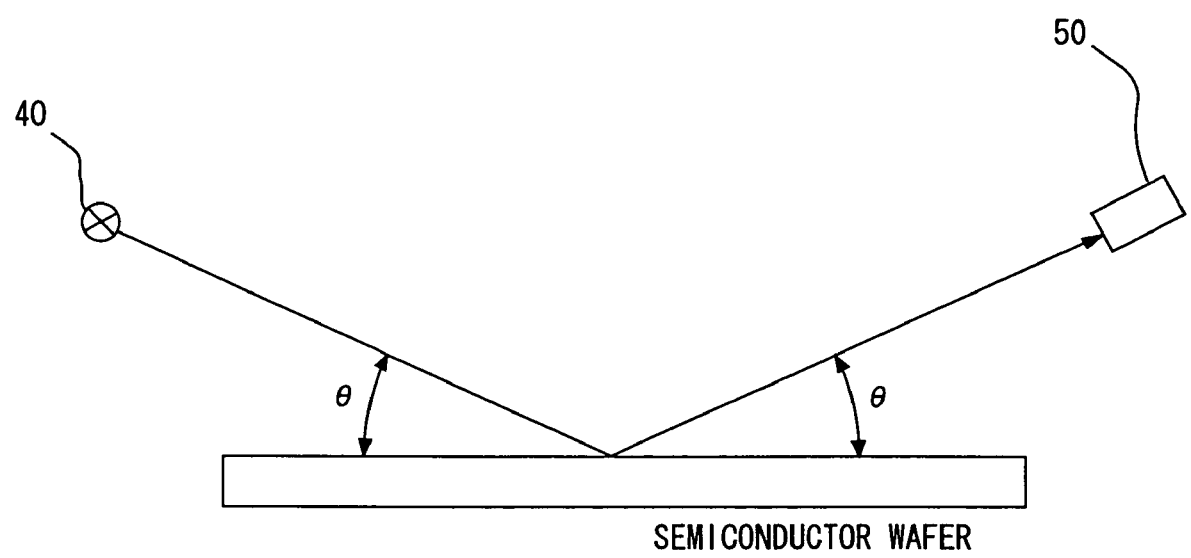
FIG. 19 is a diagram showing inclination correction of the semiconductor wafer.

Subsequently, correction of inclination of the semiconductor wafer is carried out (step S2). This inclination correction is carried out by swinging the first and second swing arms 32 and 33 of the goniometer 30 while the semiconductor wafer is fixed. When the incident angle of X-rays irradiated from the X-ray irradiation unit 40 to the semiconductor wafer is equal to θ, the X-rays are reflected from the surface of the semiconductor wafer at an angle of θ. The reflection X-rays are detected by the X-ray detector 50. At this time, if the semiconductor wafer is in horizontal position (i.e., the semiconductor wafer is not inclined) as shown in FIG. 19 with respect to the X-ray irradiation unit 40 and the X-ray detector 50, the detection value of the X-ray detector 50 becomes a peak value. On the other hand, if the semiconductor wafer is displaced from the horizontal position (the semiconductor wafer is inclined) with respect to the X-ray irradiation unit 40 and the X-ray detector 50, the detection value of the X-ray detector 50 does not become a peak value. That is, when the X-ray irradiation unit 40 and the X-ray detector 50 are swung while keeping the positional relationship therebetween under the state that the semiconductor wafer is fixed, the position of the semiconductor wafer with respect to the X-ray irradiation unit 40 and the X-ray detector 50 when the detection value of the X-ray detector 50 becomes a peak value can be regarded as the horizontal position. That is, when the output of the X-ray detector 50 is a peak value, the X-ray irradiation unit 40 and the X-ray detector 50 are arranged at the same angular position with respect to the surface of the semiconductor wafer, and with this positional arrangement as an origin, the angle control is carried out on each of the X-ray irradiation unit 40 and the X-ray detector 50.

After the measurement target site of the semiconductor wafer is positioned and the inclination correction is carried out as described above, the X-ray inspection is carried out by the X-ray reflectivity measurement (XRR), the X-ray fluorescent light measurement (XRF) or the X-ray diffraction measurement (XRD) (step S3), and the central processing unit analyzes the inspection data (step S4) and outputs an analysis result (step S5).

The above steps are carried out on all the measurement target sites set on the semiconductor wafer (step S6), and the processing is finished after the inspection of all the measurement target sites is finished.

Semiconductor Manufacturing System:

Next, a semiconductor manufacturing system in which the X-ray inspection apparatus thus constructed is installed will be described.

Figure 20:
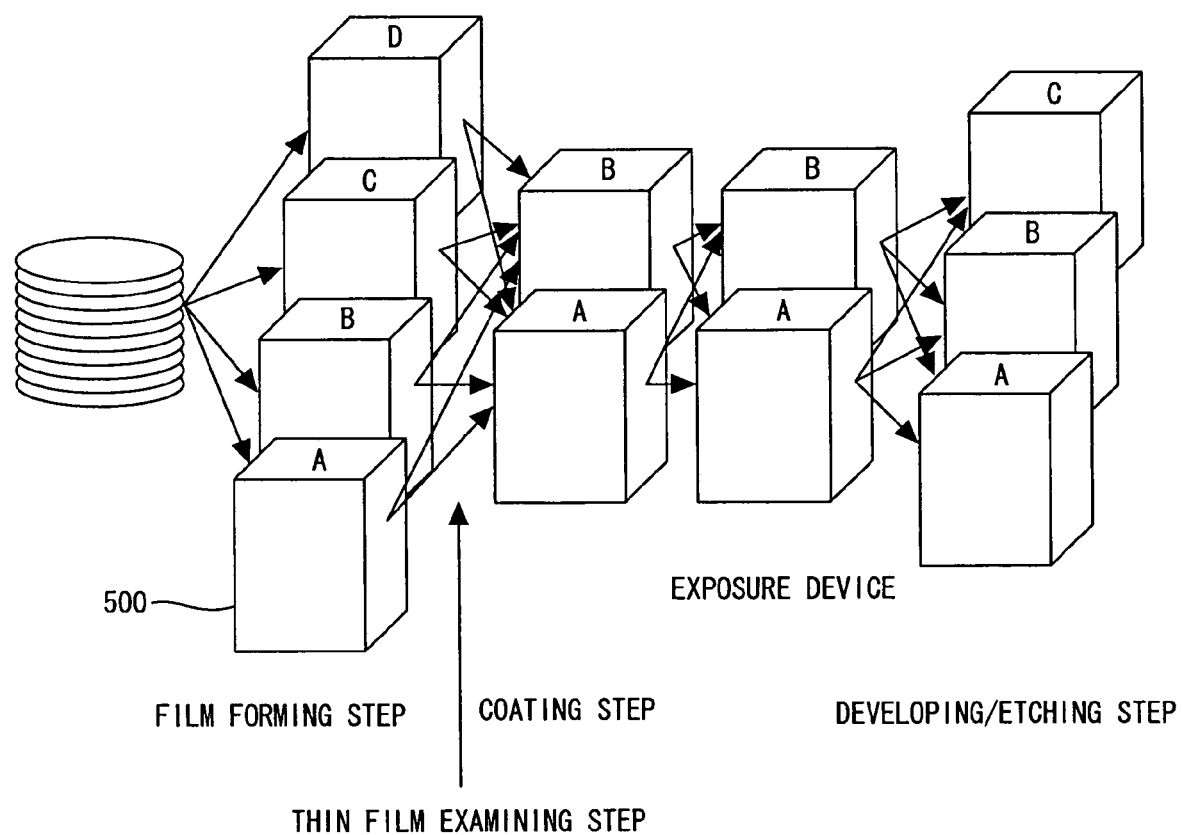
FIG. 20 is a diagram showing the construction of a part of a semiconductor manufacturing line.

FIG. 20 is a diagram showing the construction of a part of a semiconductor manufacturing line. The semiconductor manufacturing line contains a film forming step of forming thin film on the surface of the semiconductor wafer by a film forming device 500, a coating step of coating resist on the thin film, an exposure step of exposing the resist to light in conformity with a circuit pattern, a developing/etching step for the semiconductor wafer which has been subjected to exposure processing, etc.

A thin film inspection step using the X-ray inspection apparatus of this embodiment is inserted after the film forming step, and each semiconductor wafer on which film is formed by the film forming device 500 is examined in-line. The semiconductor wafer used for the inspection is not a blanket wafer, but a product wafer manufactured as a product.

The inspection is divided into an inspection for monitoring and an inspection for analysis, for example, and the inspection for monitoring is normally carried out. The inspection for monitoring is carried out by setting any five to thirteen places set on the surface of the semiconductor wafer as measurement target sites. When abnormality of thin film is detected by the inspection for monitoring, the number of measurement target sites is increased to about 50 places, and the inspection for analysis is further carried out, thereby achieving detailed thin film data.

Figure 21:
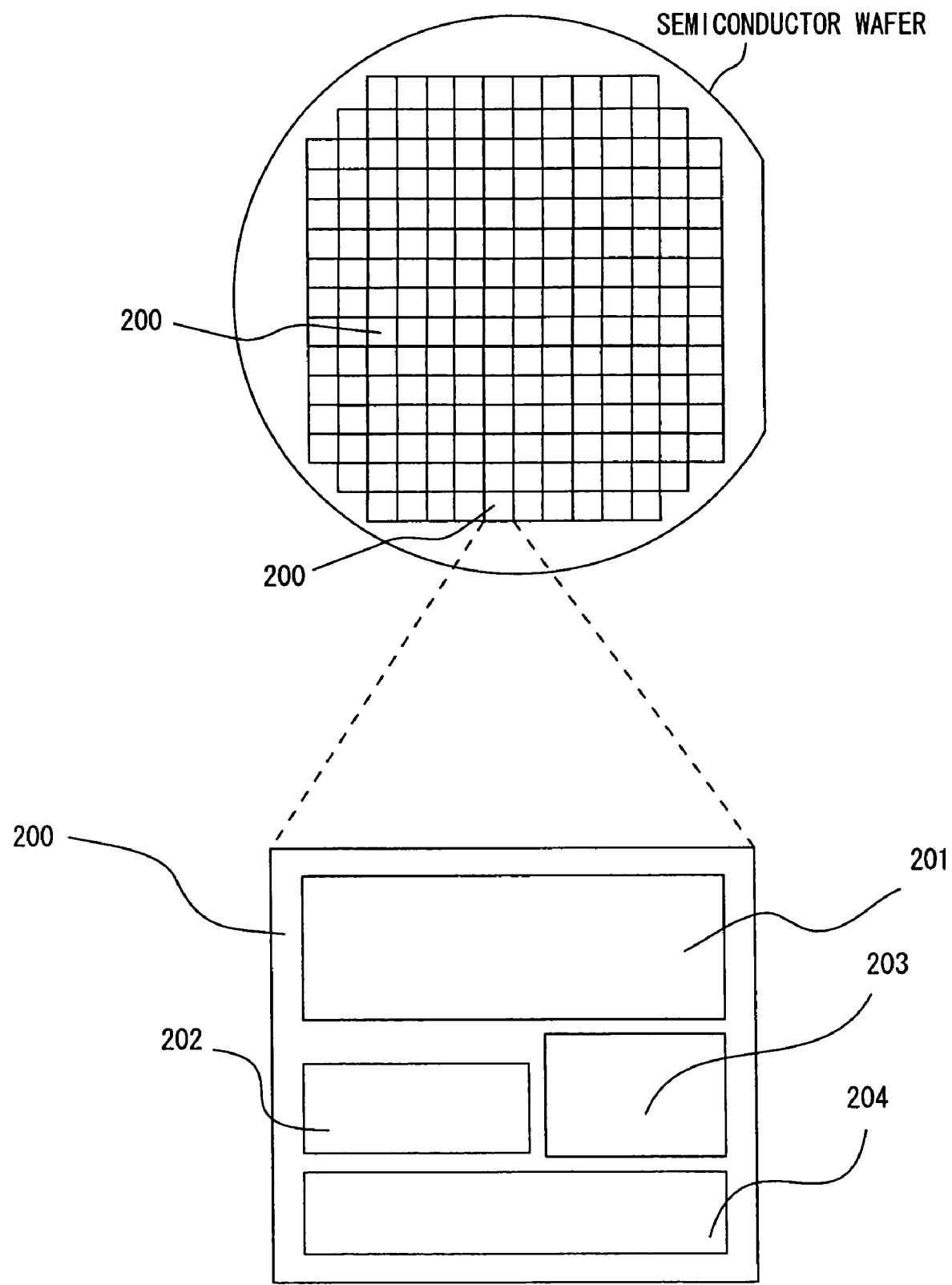
FIG. 21 is a diagram showing the internal construction of a semiconductor device formed on a semiconductor wafer, which serves as a measurement target site.

Here, a plurality of semiconductor devices 200 each of which has the same structure as shown in FIG. 21 are formed on each semiconductor wafer (product wafer), and various kinds of minute patterns such as a scribe line, a memory portion, a dummy pattern, an IC chip, etc. are formed in each semiconductor device 200 in the film forming step. Product information on various kinds of minute patterns as described above (for example, information on the position, the film thickness, the film density, etc.) is stored in a storage device in advance, and used for abnormality detection, re-inspection, etc. in the X-ray inspection step.

A product wafer from the film forming step is subjected to thin film inspection by using the X-ray inspection apparatus. At this time, when an inspection result is judged as being out of a predetermine normality judging range, the inspection site at the same place (the same position of the same thin film pattern of the same semiconductor device on the semiconductor wafer) is set as a new measurement target site and the X-ray inspection is carried out at this site again for check. At this time, by emitting an alarm from a communication unit or the like, it may be informed to an operator or the like that the manufacturing state of the semiconductor devices is under abnormality (i.e., the first inspection is abnormal). Alternatively, when an inspection result is judged as being out of the predetermined normality judging range, a site which is different from a normal site (for example, a predetermined place of the same thin film pattern of another semiconductor device on the same product wafer) is automatically indicated as a measurement target site, the positioning mechanism is controlled on the basis of the pattern recognition result from the pattern recognition unit to position the measurement target site to a predetermined measurement position, and then thin film inspection is newly carried out on the measurement target site. In this case, by emitting an alarm from the communication unit, it may be informed to the operator or the like that the manufacturing state of the semiconductor device is under abnormality (i.e., the first inspection is abnormal).

If it is judged on the basis of the inspection data thus achieved that the film forming apparatus is under abnormality, an alarm is immediately emitted by the communication unit, and the film forming device is manually checked or the feedback control operation of returning the film forming device to the normal state by changing operation parameters of the film forming device is carried out. Through this operation, a semiconductor wafer manufacturing processing having a high yield can be implemented.

Furthermore, the X-ray inspection is carried out every film forming step while minute patterns such as a scribe line, a memory portion, a dummy pattern, a specific site of an IC chip, etc. of a semiconductor device formed on a semiconductor wafer every film forming step are set as measurement target sites, and the film formation is monitored. The X-ray thin film inspection apparatus of this embodiment can irradiate X-rays having strong intensity to a minute focal point, and thus can properly irradiate X-rays to an element portion having a small area, so that thin film at a specific site can be examined. The positioning of the minute pattern to the measurement position is carried out by controlling the positioning mechanism 20 on the basis of the image picked up by the optical camera 70. At this time, it is preferable that the longitudinal direction of the minute pattern is made coincident with the X-ray incident direction. This is because the X-ray reflectivity measurement method (XRR) irradiates X-rays to a wafer serving as a sample at a minute angle (0 to 10 degrees) and thus the measurement site is expanded in the X-ray beam direction. Even when the X-ray beam of 100 µm in diameter is used, the length of a portion being examined is equal to about 2 mm at an X-ray incident angle of about 3 degrees.

As shown in FIG. 21, the inside of each semiconductor device 200 formed on the semiconductor wafer is divided into thin films having various functions, and they are formed of different thin films to achieve various characteristics. For example, respective patterns of a memory 201, a processor unit 202, a memory managing unit 203 and an interface 204 are shown in FIG. 21. Formation sites of thin film patterns to which management and inspection are needed are set as measurement target sites, and the longitudinal direction of each thin film pattern is matched with the expansion direction based on the X-ray minute angle. Accordingly, the sample table is required to be rotatable by 180 degrees or more.

Furthermore, the size of the semiconductor device 200 is generally equal to about 0.3 to 20 mm, however, the size of the thin film pattern of each measurement target site may be equal to 200 μm or less in the lateral (short side) direction. Therefore, it is desired that the X-ray beam size is equal to 200 μm or less.

Figure 22:
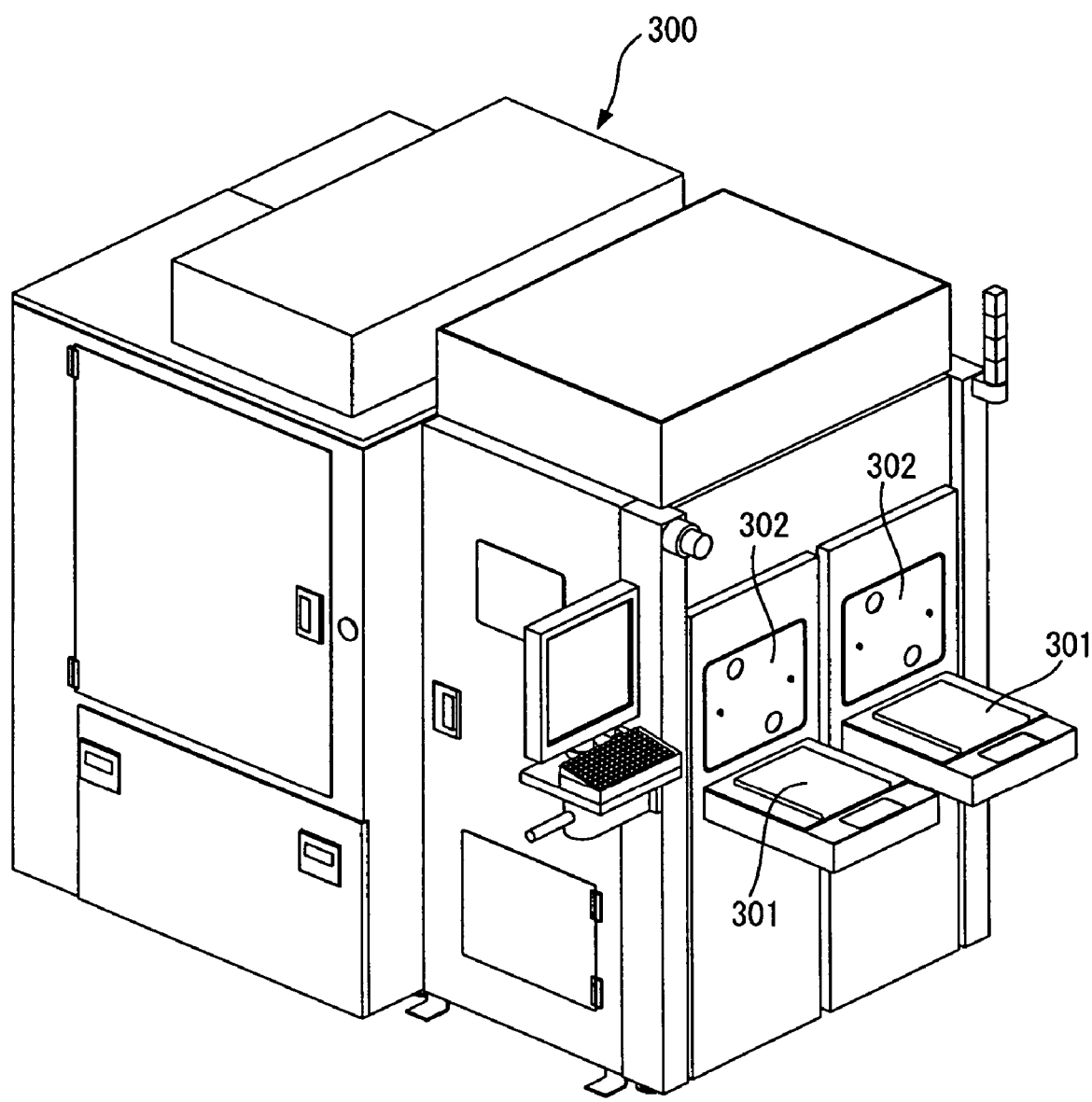
FIG. 22 is a perspective view showing a state where the X-ray inspection apparatus according to the embodiment of the present invention is covered by a cover.

As shown in FIG. 22, the X-ray inspection apparatus is disposed in a box-shaped apparatus cover 300. The apparatus cover 300 is formed of metal material for blocking X-rays. The inside of the apparatus cover 300 is sectioned into an X-ray inspection portion and a wafer feeding portion, and the X-ray inspection apparatus is disposed in the X-ray inspection portion.

The wafer feeding portion is provided with a feeding robot (not shown) for grasping semiconductor wafers one by one and automatically disposing each semiconductor wafer thus grasped on the sample table 10 of the X-ray inspection apparatus. A wafer throw-in table 301 and an insertion port 302 are provided at the front side of the apparatus cover 300, and a plurality of semiconductor wafers on which thin films have been formed by the film forming apparatus 500 are accommodated in a case with being stacked, and disposed on the wafer throw-in table 301. The feeding robot picks up the semiconductor wafers one by one from the case disposed on the wafer throw-in table 301, and feeds the semiconductor wafer this picked up to the sample table 10 of the X-ray inspection apparatus. Furthermore, the feeding robot picks up from the sample table 10 a semiconductor wafer which has been examined, and returns it onto the wafer throw-in table 301.

Main Action and Effect of the X-ray Thin Film Inspection Apparatus According to this Embodiment:

According to the X-ray thin film inspection apparatus of this embodiment, high throughput and high resolution can be implemented, and product wafers can be directly examined in line.

In the X-ray reflectivity measurement, not only the film thickness, density and roughness of a single film, but also the film thickness, density and roughness of each of several layers can be simultaneously achieved from the surface thereof. In addition, plural X-ray irradiation units 40 can be mounted on the first swing arm 32, and thus high-precision multi-layer analysis using X-ray beams having plural different wavelengths can be implemented.

In the fluorescent X-ray measurement, the CCD camera for pattern recognition and the fluorescent X-ray detector can be positionally moved, and thus the fluorescent X-ray detector can be disposed in proximity to the sample wafer. Accordingly, the film thickness of aluminum film can be measured under atmospheric air in addition to Cu and Ta. In the case of aluminum, fluorescent X-rays are absorbed by air and thus the intensities thereof are weak, so that it has been difficult to measure the film thickness of aluminum film by the conventional system. According to the X-ray thin film inspection apparatus of this embodiment, the fluorescent X-rays can be captured at high sensitivity and the film thickness of the aluminum film can be measured.

That is, when an inspection condition is set in the aluminum measurement operation, the first swing arm 32 is swung so that an X-ray irradiation unit 40 for generating X-rays having a wavelength suitable for the measurement of aluminum is disposed at an incident angle position of a low angle with respect to a semiconductor wafer to be examined.

Specifically, the incident angle is set to 1 degree to 5 degrees. In detail, when the incident angle is represented by θ degree and the film thickness of the aluminum film at the measurement target site of the semiconductor wafer is represented by tμm, the incident angle is preferably set so as to satisfy the relational expression: sin θ=t/27.

By setting the incident angle to a low angle as described above, a margin space in which the incident X-rays to the semiconductor wafer is not blocked by the fluorescent X-ray detector 60 can be formed. Accordingly, the fluorescent X-ray detector 60 can be downwardly moved by a vertically moving mechanism contained in the equipment exchange mechanism 80 so that the fluorescent X-ray detector 60 can be disposed to be closer to the surface of the semiconductor wafer as compared with the measurement of other elements.

Accordingly, the X-ray passage (the X-ray incident space) between the measurement face of the semiconductor wafer and the fluorescent X-ray detector can be set to 1 to 2 mm, and the fluorescent X-ray detector 60 can capture the fluorescent X-rays before lots of fluorescent X-rays occurring from the measurement face of the semiconductor wafer are absorbed by air. When the incident angle is set to 1 degree, the X-ray passage can be set to 1 mm.

A described above, the X-ray irradiation unit 40 for generating X-rays having a wavelength suitable for the measurement of aluminum is disposed at the incident angle position of a low angle with respect to the semiconductor wafer under inspection by the first swing arm 32, and also the fluorescent X-ray detector 60 can be downwardly moved by a vertically moving mechanism contained in the equipment exchange mechanism 80 so that the fluorescent X-ray detector 60 can be disposed to be closer to the surface of the semiconductor wafer as compared with the measurement of other elements. Accordingly, the intensity of the fluorescent X-rays occurring from the aluminum film can be suppressed from being attenuated until the fluorescent X-rays reach the fluorescent X-ray detector 60, so that it is possible to measure the film thickness of aluminum film under atmospheric air.

Furthermore, a minute area to be examined can be measured at a minute pitch, and thus an in-plane distribution of film thickness can be measured with high resolution. The X-ray thin film inspection apparatus of the present invention can be also used to measure a wafer edge portion, and thus it can exercise its power in high throughput and high resolution measurements not only when it is used as film thickness monitor, but also when it is used to newly start a film forming process.

What is claimed is:

1. An X-ray thin film inspection apparatus comprises:
   a sample table for disposing an inspection target on the upper surface thereof;
   a pattern recognition unit for recognizing an image of the inspection target disposed on the upper surface of the sample table;
   a positioning mechanism that is controlled on the basis of a pattern recognition result of the inspection target achieved by the pattern recognition unit and moves the sample table in two directions orthogonal to each other on any plane, a direction perpendicular to the plane concerned and an in-plane rotational direction of the plane concerned;
   a goniometer having first and second swing members swinging along a virtual plane perpendicular to the upper surface of the sample table;
   at least one X-ray irradiation unit that is mounted on the first swing member and has an X-ray tube and an X-ray optical element mounted in the main body of the X-ray irradiation unit; and an X-ray detector mounted on the second swing member.

2. The X-ray thin film inspection apparatus according to claim 1, wherein the X-ray optical element of the X-ray irradiation unit has a function of leading X-rays irradiated from the X-ray tube to a preset measurement position while converging the X-rays thus irradiated into a cross-sectional shape of 200 μm or less in diameter.

3. The X-ray thin film inspection apparatus according to claim 1, wherein the X-ray irradiation unit has a shutter for interrupting or passing therethrough the X-rays irradiated from the X-ray tube to lead the X-rays to the X-ray optical element in the main body of the X-ray irradiation unit, and a gas flow passage is formed around the shutter.

4. The X-ray thin film inspection apparatus according to claim 1, wherein the X-ray detector comprises an avalanche photodiode (APD).

5. The X-ray thin film inspection apparatus according to claim 1, wherein plural X-ray irradiation units are mounted on the first swing member so as to be arranged in the swing direction.

6. The X-ray thin film inspection apparatus according to claim 5, wherein the plural X-ray irradiation units contain X-ray tubes for generating X-rays having different wavelengths.

7. The X-ray thin film inspection apparatus according to claim 1, further comprising a fluorescent X-ray detector for detecting fluorescent X-rays generated from the inspection target by irradiating X-rays.

8. The X-ray thin film inspection apparatus according to claim 7, wherein the pattern recognition unit comprises an optical camera and a pattern recognition circuit for recognizing an image taken by the optical camera, and the optical camera and the fluorescent X-ray detector are disposed above the sample table, and the X-ray thin film inspection apparatus is further equipped with an equipment exchange mechanism for selecting one of the optical camera and the fluorescent X-ray detector and moving the selected one element of the optical camera and the fluorescent X-ray detector so that the selected one element faces a predetermined measurement position.

9. The X-ray thin film inspection apparatus according to claim 8, further comprising a cover member for covering the optical camera, the fluorescent X-ray detector and the equipment exchange mechanism, the cover member being formed with a transmission window so that the transmission window faces the visual field of the optical camera, and an exhaust unit for exhausting gas in the inner space formed by the cover.

10. The X-ray thin film inspection apparatus according to claim 1, wherein the inspection target is a product wafer on which a plurality of semiconductor devices having the same structure including various kinds of minute thin film patterns are formed, a minute thin film pattern of a predetermined semiconductor device formed on the product wafer concerned is set as a measurement target site, and the X-ray thin film inspection apparatus is further equipped with a controller for controlling the positioning mechanism on the basis of a recognition result from the pattern recognition unit to position the measurement target site to a predetermined measurement position and carrying out thin film inspection on the measurement target site.

11. The X-ray thin film inspection apparatus according to claim 10, wherein the controller further controls the positioning mechanism on the basis of the recognition result from the pattern recognition unit to position the measurement target site so that the longitudinal direction of the measurement target site is coincident with the incident direction of the X-rays from the X-ray irradiation unit.

12. The X-ray thin film inspection apparatus according to claim 10, wherein when the inspection result of the measurement target site is out of a predetermined normality judging range, the controller sets the same measurement target site of the same thin film pattern of the same semiconductor device on the product wafer as a new measurement target site and carries out thin film inspection on the measurement target site thus newly set again.

13. The X-ray thin film inspection apparatus according to claim 10, wherein when the inspection result of the measurement target site is out of a predetermined normality judging range, the controller sets any site of the same thin film pattern of a different semiconductor device on the product wafer as a measurement target site, controls the positioning mechanism on the basis of the recognition result from the pattern recognition unit to position the measurement target site to a predetermined measurement position, and carries out thin film inspection on the measurement target site.

14. A product wafer thin film inspection apparatus comprises:
an X-ray thin film inspection apparatus including a sample table for disposing an inspection target on the upper surface thereof, a pattern recognition unit for recognizing an image of the inspection target disposed on the upper surface of the sample table, a positioning mechanism that is controlled on the basis of a pattern recognition result of the inspection target achieved by the pattern recognition unit and moves the sample table in two directions orthogonal to each other on any plane, a direction perpendicular to the plane concerned and an in-plane rotational direction of the plane concerned, a goniometer having first and second swing members swinging along a virtual plane perpendicular to the upper surface of the sample table, at least one X-ray irradiation unit that is mounted on the first swing member and has an X-ray tube and an X-ray optical element mounted in the main body of the X-ray irradiation unit, and an X-ray detector mounted on the second swing member;
a feeding robot for feeding thin-film-formed semiconductor wafers in a semiconductor manufacturing process to the sample table of the X-ray thin film inspection apparatus one by one; and
a mount cover in which the X-ray thin film inspection apparatus and the feeding robot are accommodated.

15. A product wafer thin film inspection method using an X-ray thin film inspection apparatus including a sample table for disposing an inspection target on the upper surface thereof, a pattern recognition unit for recognizing an image of the inspection target disposed on the upper surface of the sample table, a positioning mechanism that is controlled on the basis of a pattern recognition result of the inspection target achieved by the pattern recognition unit and moves the sample table in two directions orthogonal to each other on any plane, a direction perpendicular to the plane concerned and an in-plane rotational direction of the plane concerned, a goniometer having first and second swing members swinging along a virtual plane perpendicular to the upper surface of the sample table, at least one X-ray irradiation unit that is mounted on the first swing member and has an X-ray tube and an X-ray optical element mounted in the main body of the X-ray irradiation unit, and an X-ray detector mounted on the second swing member, comprises the steps of:

setting a minute thin film pattern of a semiconductor device formed on a product wafer as a measurement target site;

positioning the measurement target site to a measurement position of the X-ray thin film inspection apparatus; and carrying out thin film inspection on the measurement target site.

16. The product wafer thin film inspection method according to claim 15, wherein the thin film inspection of the measurement target site is carried out while the longitudinal direction of the measurement target site is coincident with the incident direction of the X-rays from the X-ray irradiation unit.

17. The X-ray thin film inspection method according to claim 15, wherein when the inspection result of the measurement target site is out of a predetermined normal range which is judged as being normal, the same measurement target site of the same thin film pattern of the same semiconductor device on the product wafer is set as a new measurement target site and thin film inspection is carried out on the measurement target site thus newly set again.

18. The X-ray thin film inspection method according to claim 15, wherein when the inspection result of the measurement target site is out of a predetermined normal range which is judged as being normal, any site of the same thin film pattern of a different semiconductor device on the product wafer is set as a measurement target site, the positioning mechanism is controlled on the basis of the recognition result from the pattern recognition unit to position the measurement target site to a predetermined measurement position, and thin film inspection is carried out on the measurement target site.

* * * * *